US012734192B1

(12) United States Patent
Moshal et al.

(10) Patent No.: US 12,734,192 B1
(45) Date of Patent: Sep. 15, 2026

(54) PHARMACEUTICAL POWDER COMPOSITIONS INCLUDING POTASSIUM CHLORIDE AND METHODS OF MAKING AND USING THE SAME

(71) Applicant: GENUS LIFESCIENCES INC., Allentown, PA (US)

(72) Inventors: Jeffrey M. Moshal, Allentown, PA (US); Michael Libman, Southampton, PA (US)

(73) Assignee: GENUS LIFESCIENCES INC., Allentown, PA (US)

( * ) Notice: Subject to any disclaimer, the term of this patent is extended or adjusted under 35 U.S.C. 154(b) by 0 days.

(21) Appl. No.: 19/411,523

(22) Filed: Dec. 8, 2025

Related U.S. Application Data

(63) Continuation of application No. 18/791,715, filed on Aug. 1, 2024.

(60) Provisional application No. 63/518,037, filed on Aug. 7, 2023.

(51) Int. Cl.

| | |
|---|---|
| *A61K 8/24* | (2006.01) |
| *A61K 8/02* | (2006.01) |
| *A61K 8/9789* | (2017.01) |
| *A61K 9/00* | (2006.01) |
| *A61K 33/14* | (2006.01) |
| *A61K 47/02* | (2006.01) |
| *A61K 47/12* | (2006.01) |
| *A61K 47/26* | (2006.01) |
| *A61Q 11/00* | (2006.01) |

(52) U.S. Cl.
CPC ............ *A61K 33/14* (2013.01); *A61K 9/0095* (2013.01); *A61K 47/02* (2013.01); *A61K 47/12* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,970,750 A | 7/1976 | Brockemeyer et al. | |
| 4,259,315 A | 3/1981 | Lippmann et al. | |
| 4,259,323 A | 3/1981 | Ranucci | |
| 4,352,791 A | 10/1982 | Zaffaroni et al. | |
| 4,582,705 A | 4/1986 | Primes et al. | |
| 4,723,957 A | 2/1988 | Magruder et al. | |
| 4,747,847 A | 5/1988 | Magruder et al. | |
| 5,035,898 A | 7/1991 | Chang et al. | |
| 5,066,483 A | 11/1991 | Harkrader et al. | |
| 5,284,648 A | 2/1994 | White et al. | |
| 5,449,522 A | 9/1995 | Hill | |
| 5,505,962 A | 4/1996 | Sparks | |
| 5,780,055 A | 7/1998 | Habib et al. | |
| 6,199,698 B1 * | 3/2001 | Hetrick | B65D 75/5855 206/532 |
| 6,365,182 B1 | 4/2002 | Khankari et al. | |
| 6,780,437 B2 | 8/2004 | Christenson et al. | |
| 6,793,935 B2 | 9/2004 | Hermelin et al. | |
| 6,899,899 B2 | 5/2005 | Takagi et al. | |
| 7,056,534 B2 | 6/2006 | Christenson et al. | |
| 7,189,415 B2 | 3/2007 | Takagi et al. | |
| 7,566,463 B2 | 7/2009 | Ayala | |
| 8,685,483 B2 | 4/2014 | Knight | |
| 8,691,190 B2 | 4/2014 | Haught et al. | |
| 8,771,749 B2 | 7/2014 | Oda et al. | |
| 9,763,464 B2 | 9/2017 | Hoejvang-Nielsen | |
| 9,795,636 B2 | 10/2017 | Oda et al. | |
| 11,071,739 B1 | 7/2021 | Parikh | |
| 12,539,314 B1 | 2/2026 | Phadke et al. | |
| 2002/0031547 A1 | 3/2002 | Takagi et al. | |
| 2003/0072719 A1 | 4/2003 | Nelson et al. | |
| 2003/0104070 A1 | 6/2003 | Christenson et al. | |
| 2003/0108605 A1 | 6/2003 | Hermelin et al. | |
| 2005/0170020 A1 | 8/2005 | Medasani et al. | |
| 2007/0014856 A1 | 1/2007 | Takagi et al. | |
| 2009/0017167 A1 | 1/2009 | Krumhar et al. | |
| 2010/0303853 A1 | 12/2010 | Lejeune et al. | |
| 2011/0300266 A1 | 12/2011 | Rinaldi et al. | |
| 2012/0003163 A1 | 1/2012 | Mordas | |
| 2015/0290112 A1 | 10/2015 | Nesta et al. | |
| 2017/0056441 A1 | 3/2017 | Adeniji et al. | |
| 2017/0333561 A1 | 11/2017 | Alley | |
| 2019/0069578 A1 | 3/2019 | Washio | |

FOREIGN PATENT DOCUMENTS

| | | | | |
|---|---|---|---|---|
| CN | 103479664 A | 1/2014 | | |
| WO | 2017/150715 A1 | 9/2017 | | |
| WO | 2018/043275 A1 | 3/2018 | | |
| WO | WO-2023230636 A2 * | 11/2023 | ......... | A61K 36/9066 |

OTHER PUBLICATIONS

Lachance, E.V., et al., Potassium chloride caking tendency: A parametric study of cake break energy, Adv. Powder Technol., 29 (2018) pp. 2140-2152. (Year: 2018).*

Blanco, D., et al., Effect of colloidal silicon dioxide and moisture on powder flow properties: Predicting in-process performance using image-based analysis, I. J. Pharm., 597 (Feb. 2, 2021). (Year: 2021).*

FDA Prescribing Information, Potassium Chloride (Revision Jul. 2019); accessed on Mar. 7, 2026 at https://www.accessdata.fda.gov/drugsatfda_docs/label/2014/206814lbl.pdf; hereinafter, "FDA"). (Year: 2019).*

Potassium Chloride—potassium chloride solution (Pharmaceutical Associates, Inc.) (Revised: Jan. 2015).

Potassium Chloride—potassium chloride solution (Amneal Pharmaceuticals LLC) (Revised: Jun. 2017).

Potassium Chloride—potassium chloride solution (Apotex Corp) (Revised: Feb. 2018).

Potassium Chloride oral solution (Genus Lifesciences Inc.) (Revised: Feb. 2019).

Potassium Chloride—potassium chloride solution (Lupin Pharmaceuticals, Inc.) (Revised: Oct. 2018).

Potassium Chloride—potassium chloride solution (Novel Laboratories, Inc.) (Revised: Nov. 2018).

Potassium Chloride—potassium chloride solution (Par Pharmaceutical) (Revised: Apr. 2018).

(Continued)

*Primary Examiner* — Dominic Lazaro
(74) *Attorney, Agent, or Firm* — K&L Gates LLP

(57) ABSTRACT

Pharmaceutical powder compositions including potassium chloride and methods of making and using the pharmaceutical powder compositions are disclosed.

17 Claims, 6 Drawing Sheets

(56) References Cited

OTHER PUBLICATIONS

Potassium Chloride—potassium chloride solution (VistaPharm, Inc.) (Revised: Jun. 2017).
Potassium Chloride Oral Solution, USP 20%, https://dailymed.nlm.nih.gov/dailymed/fda/fdaDrugXsl.cfm?setid=6d2cec16-3127-49b5-9cb1-840 . . . , accessed Jan. 11, 2019, 6 pages.
Prescribing Information, K-10, Potassium Chloride Oral Solution, 10% USP, Potassium Replacement Therapy, GlaxoSmithKline Inc., Ontario, Canada, Aug. 30, 2017, 10 pages.
Potassium Chloride Oral Solution, USP, https://dailymed.nlm.nih.gov/dailymed/fda/fdaDrugXsl.cfm?setid=aacd46d1-8e11-4a82-80bb-a9c . . . , accessed Jan. 11, 2019, 3 pages.
Ogochukwu et al. "Effect of some preservatives on the aqueous stability of an oral rehydration salt solution intended for use in developing countries," Asian Journal of Pharmaceutical and Clinical Research, 6(2):33-37, 2013.
Allen et al., "Proabsorptive effect of glycerol as a glucose substitute in oral rehydration solutions", Journal of Nutritional Biochemistry, 10:49-55, 1999.
Barreuther et al., "Palatability comparison of oral potassium chloride solutions", American Journal of Hospital Pharmacy 34:1090-1092, 1977.
USPTO artificial intelligence top results, printed 2025.
Joshi et al., "Concentration, temperature, and pH dependence of sunset-yellow aggregates in aqueous solutions: An x-ray investigation", Physical Review E 80, 041703-1-041703-8, 2009.
U.S. Appl. No. 16/295,215, filed Mar. 7, 2019.
U.S. Appl. No. 17/660,499, filed Apr. 25, 2022.
U.S. Appl. No. 19/438,952, filed Jan. 2, 2026.
U.S. Appl. No. 18/791,715, filed Aug. 1, 2024.
USPTO artificial intelligence top results, printed 2026.

* cited by examiner

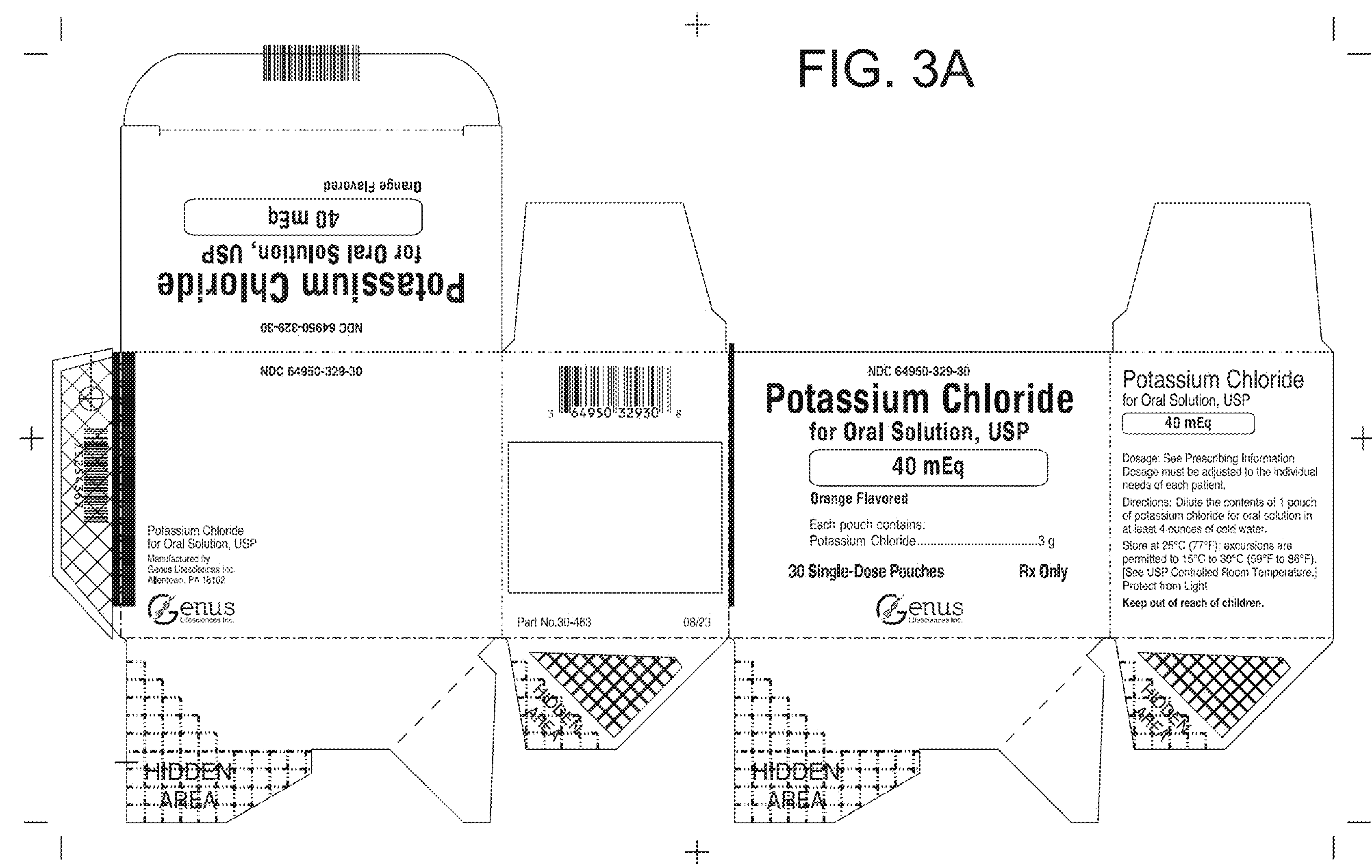
FIG. 3A
NDC 64950-329-30
Potassium Chloride
for Oral Solution, USP
40 mEq
Orange Flavored
NDC 64950-329-30
Potassium Chloride
for Oral Solution, USP
Manufactured by
Genus Lifesciences Inc.
Allentown, PA 18102
Genus Lifesciences Inc.
HIDDEN AREA
5 64950 32930 8
Part No.36-463
08/23
HIDDEN AREA
NDC 64950-329-30
Potassium Chloride
for Oral Solution, USP
40 mEq
Orange Flavored
Each pouch contains:
Potassium Chloride.....3 g
30 Single-Dose Pouches
Rx Only
Genus Lifesciences Inc.
HIDDEN AREA
Potassium Chloride
for Oral Solution, USP
40 mEq
Dosage: See Prescribing Information. Dosage must be adjusted to the individual needs of each patient.
Directions: Dilute the contents of 1 pouch of potassium chloride for oral solution in at least 4 ounces of cold water.
Store at 25°C (77°F); excursions are permitted to 15°C to 30°C (59°F to 86°F). [See USP Controlled Room Temperature.] Protect from Light
Keep out of reach of children.
HIDDEN AREA Potassium Chloride
for Oral Solution, USP
40 mEq
Orange Flavored
100 Single-Dose Pouches
Rx Only
HIDDEN AREA
HIDDEN AREA
HIDDEN AREA
HIDDEN AREA

PHARMACEUTICAL POWDER COMPOSITIONS INCLUDING POTASSIUM CHLORIDE AND METHODS OF MAKING AND USING THE SAME

FIELD OF THE TECHNOLOGY

The present disclosure relates to pharmaceutical powder compositions comprising potassium chloride and to methods of making and using the pharmaceutical powder compositions.

CROSS-REFERENCE TO RELATED APPLICATIONS

The present application claims priority under 35 U.S.C. § 120 as a continuation of co-pending U.S. application Ser. No. 18/791,715, filed Aug. 1, 2024, which claims the benefit of U.S. Provisional Application No. 63/518,037, filed Aug. 7, 2023, the entire disclosures of which are hereby incorporated by reference in their entirety.

DESCRIPTION OF THE BACKGROUND OF THE TECHNOLOGY

Potassium chloride is known in the art for the treatment and prophylaxis of hypokalemia. While potassium chloride can be administered as oral solid tablets, high concentrations of potassium chloride, as can be included in solid oral tablets, may produce gastric upset. To minimize gastric upset, potassium chloride can be administered as an oral solution. Oral potassium chloride solutions, however, also present drawbacks. For example, while solid oral tablets are not particularly vulnerable to bacterial contamination, oral solutions may be. Conventionally, bacterial contamination of an oral liquid formulation is inhibited by adding a bacteriostatic or bactericidal amount of ethanol. However, the safety of alcohol as an excipient in pharmaceuticals intended for use in children, and particularly those intended for use in very young children, is a significant concern, even when relatively low alcohol concentrations (e.g., less than 0.5 vol. %) are present.

Accordingly, there is a need for an improved pharmaceutical powder composition that exhibits advantageous stability and improved shelf life, wherein the powder can be combined with water to form an oral solution, and wherein the oral solution can be resistant to bacterial contamination.

SUMMARY

It is understood that the inventions disclosed and described in this specification are not limited to the embodiments described in this Summary.

One non-limiting aspect according to the present disclosure is directed to a pharmaceutical powder composition comprising, by weight: about 90% to about 99.5% potassium chloride; and about 0.5% to about 1.5% colloidal silicon dioxide. In various non-limiting embodiments, the pharmaceutical powder composition is stable such that, for example, a total content of potassium chloride in a volume of the pharmaceutical powder composition is at least 90%, at least 92%, at least 95%, at least 97%, or at least 99% of an original total content of potassium chloride after the volume of the pharmaceutical powder composition is stored for 6 months, 9 months, 24 months, 36 months, or 48 months at a temperature of about 23° C. to about 27° C. and a relative humidity of about 55% to about 65%, or is stored for 3 months or 6 months at a temperature of about 38° C. to about 42° C. and a relative humidity of about 70% to about 80%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 6 months at about 23° C. to about 27° C. and a relative humidity of about 55% to about 65%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content in the volume after the pouch or other container containing the volume of the pharmaceutical powder composition has been stored for 9 months at about 23° C. to about 27° C. and a relative humidity of about 55% to about 65%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 24 months at about 23° C. to about 27° C. and a relative humidity of about 55% to about 65%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 36 months at about 23° C. to about 27° C. and a relative humidity of about 55% to about 65%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 48 months at about 23° C. to about 27° C. and a relative humidity of about 55% to about 65%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 3 months at about 38° C. to about 42° C. and a relative humidity of about 70% to about 80%.

An additional non-limiting embodiment according to the present disclosure is directed to a packaged pharmaceutical powder product comprising: a pharmaceutical powder composition comprising, by weight, about 90% to about 99.5% potassium chloride, and about 0.5% to about 1.5% colloidal silicon dioxide; and a pouch or other container; provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 6 months at about 38° C. to about 42° C. and a relative humidity of about 70% to about 80%.

An additional non-limiting embodiment according to the present disclosure is directed to an aqueous oral composition made by combining ingredients comprising: a pharmaceutical powder composition comprising, by weight, about 90% to about 99.5% potassium chloride, and about 0.5% to about 1.5% colloidal silicon dioxide; and water.

An additional non-limiting embodiment according to the present disclosure is directed to a method of treating hypokalemia or another medical condition, the method comprising administering an therapeutically effective amount of an aqueous oral solution to a subject in need thereof, wherein the aqueous oral solution is made by combining ingredients comprising: a pharmaceutical powder composition comprising, by weight, about 90% to about 99.5% potassium chloride, and about 0.5% to about 1.5% colloidal silicon dioxide; and water.

BRIEF DESCRIPTION OF THE DRAWINGS

Various features and characteristics of non-limiting and non-exhaustive embodiments disclosed and described in this specification may be better understood by reference to the accompanying figures, in which:

FIG. 3A shows an unassembled carton, wherein the carton is used to contain 30 single-dose pouches containing a pharmaceutical powder composition including about 40 mEq potassium chloride, as described herein.

Figure 1A:
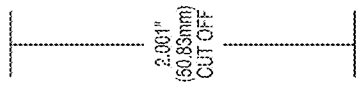
FIG. 1A shows an unassembled container in the form of an unassembled pouch, wherein the pouch is used to contain a pharmaceutical powder composition including about 10 mEq potassium chloride, as described herein.
Figure 1A:
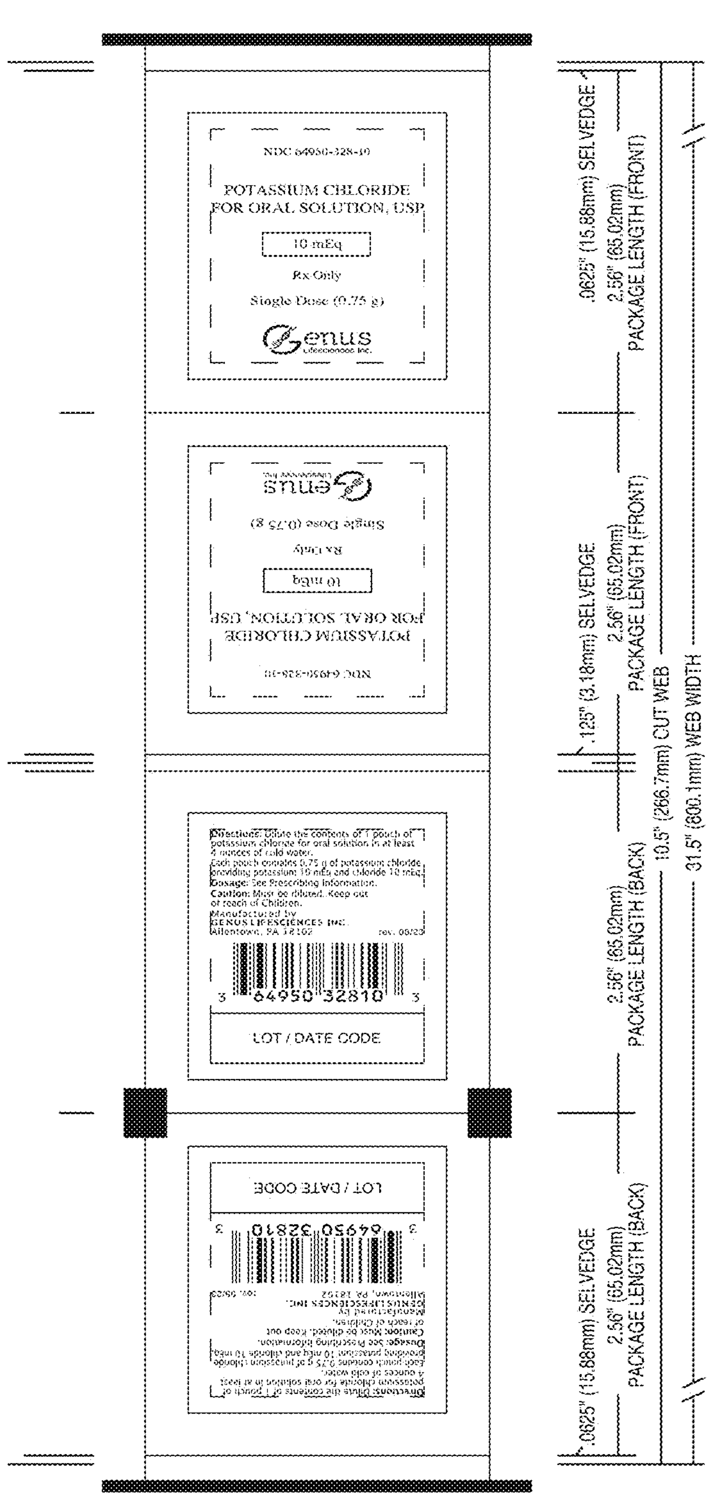

The reader will appreciate the foregoing details, as well as others, upon considering the following detailed description of various non-limiting and non-exhaustive embodiments according to the present disclosure.

DESCRIPTION OF CERTAIN NON-LIMITING EMBODIMENTS

Various embodiments are described and illustrated in this specification to provide an overall understanding of the disclosed compositions and methods. It is understood that the various embodiments described and illustrated in this specification are non-limiting and non-exhaustive. Thus, the present invention is not limited by the description of the various non-limiting and non-exhaustive embodiments disclosed in this specification. Certain features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be found present in the prior art. The various embodiments disclosed and described in this specification can comprise, consist of, or consist essentially of the features and characteristics as variously described herein.

All percentages provided herein are weight percentages based on the total weight of the respective composition, powder, tablet, mixture, etc., unless otherwise indicated.

Any numerical ranges recited in this specification are intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Applicant reserves the right to amend this specification, including the claims, to expressly recite any sub-range subsumed within the ranges expressly recited herein.

As generally used herein, the term “about” refers to an acceptable degree of error for the quantity measured, given the nature or precision of the measurement. Typical exemplary degrees of error may be within 20%, 10%, or 5% of a given value or range of values.

The terms “subject” and “patient” are used interchangeably herein, and it is intended that both refer to a recipient on whom a method is conducted according to the present disclosure or another method, as the case may be.

The terms “stability” and “stable” as used herein refer to a pharmaceutical powder composition retaining at least 90%, at least 95%, at least 97%, at least 99%, or 100% of an initial potassium chloride content in the pharmaceutical powder composition after the pharmaceutical powder composition has been stored for a period of time under indicated conditions.

Disclosed herein are pharmaceutical powder compositions comprising potassium chloride. In certain of the embodiments herein, the pharmaceutical powder composition comprises potassium chloride and colloidal silicon dioxide. Certain of the pharmaceutical powder compositions can further comprise one or more of a sweetener and citric acid. The present inventors observed that certain embodiments of the pharmaceutical powder compositions according to the present disclosure exhibit unexpectedly advantageous stability of potassium chloride in the pharmaceutical powder compositions.

The present pharmaceutical powder compositions comprise potassium chloride as an active pharmaceutical ingredient. In certain non-limiting embodiments, potassium chloride may be present in the pharmaceutical powder composition according to the present disclosure in a concentration of 90% to 99.5%, in weight percent based on the total weight of the pharmaceutical powder composition, such as, for example, 90% to 98.5%, 90% to 97.5%, 90% to 96.5%, 90% to 95.5%, 91% to 98.5%, 91% to 97.5%, 91% to 96.5%, 91% to 95.5%, 92% to 98.5%, 92% to 97.5%, 92% to 96.5%, 92% to 95.5%, 93% to 98.5%, 93% to 97.5%, 93% to 96.5%, 93% to 95.5%, 94% to 99.5%, or 92% to 99.5%, all in weight percent based on total weight of the pharmaceutical powder composition. In certain embodiments, potassium chloride may be present in the pharmaceutical powder composition in a concentration of about 90%, about 91%, about 92%, about 93%, about 94%, about 95%, about 96%, about 97%, about 98%, about 99%, about 99.5%, in weight based on the total weight of the pharmaceutical powder composition.

In certain non-limiting embodiments, depending on the desired strength of the particular pharmaceutical powder composition, the mass of potassium chloride included in a pharmaceutical powder composition according to the present disclosure can range from about 675 mg to about 825 mg, from about 700 mg to about 825 mg, from about 725 mg to about 825 mg, from about 675 mg to about 800 mg, from about 675 mg to about 775 mg, from about 700 mg to about 800 mg, from about 725 mg to about 800 mg, from about 725 mg to about 775 mg, from about 1350 mg to about 1650 mg, from about 1400 mg to about 1650 mg, from about 1450 mg to about 1650 mg, from about 1350 mg to about 1600 mg, from about 1350 mg to about 1550 mg, from about 1400 mg to about 1600 mg, from about 1400 mg to about 1550 mg, from about 1450 mg to about 1600 mg, or from about 1450 mg to about 1550 mg, from about 2700 mg to about 3300 mg, from about 2700 mg to about 3250 mg, from about 2700 mg to about 3200 mg, from about 2700 mg to about 3150 mg, from about 2700 mg to about 3100 mg, from about 2700 mg to about 3050 mg, from about 2750 mg to about 3300 mg, from about 2800 mg to about 3300 mg, from about 2850 mg to about 3300 mg, from about 2900 mg to about 3300 mg, from about 2950 mg to about 3300 mg, from about 2800 mg to about 3200 mg, from about 2900 mg to about 3100 mg, or from about 2950 mg to about 3050 mg.

Various non-limiting embodiments of a pharmaceutical powder composition according to the present disclosure can comprise one or more glidants. Glidants may be included in the pharmaceutical powder composition, for example, to enhance flowability of the powder ingredients by reducing interparticle friction, particle surface charge, and/or particle cohesion. Non-limiting examples of suitable glidants that can be included in embodiments of the pharmaceutical powder composition according to the present disclosure include talc, silicon dioxide, colloidal silicon dioxide, and combinations of any thereof.

The concentration of glidant in a pharmaceutical powder composition according to certain non-limiting embodiments of the present disclosure can range from about 0.5% to about 1.5%, from about 0.6% to about 1.5%, from about 0.75% to about 1.5%, from about 0.8% to about 1.5%, from about 0.9% to about 1.5%, from about 0.5% to about 1.4%, from about 0.5% to about 1.3%, from about 0.5% to about 1.2%, from about 0.5% to about 1.1%, from about 0.75% to about 1.25%, from about 0.85% to about 1.25%, from about 0.85% to about 1.15%, or from about 0.85% to about 1.05%, all in weight percent based on total weight of the pharmaceutical powder composition.

In certain non-limiting embodiments, the amount of glidant included in a pharmaceutical powder composition according to the present disclosure can range from about 5 mg to about 36 mg, such as from about 5 mg to about 9 mg, from about 5 mg to about 8 mg, from about 6 mg to about 9 mg, from about 6 mg to about 8 mg, from about 7 mg to about 8 mg, from about 12 mg to about 18 mg, from about 12 mg to about 17 mg, from about 12 mg to about 16 mg, from about 13 mg to about 18 mg, from about 14 mg to about 18 mg, from about 13 mg to about 17 mg, from about 13 mg to about 16 mg, from about 14 mg to about 16 mg, from about 24 mg to about 36 mg, from about 24 mg to about 34 mg, from about 24 mg to about 32 mg, from about 26 mg to about 36 mg, from about 26 mg to about 34 mg, from about 26 mg to about 32 mg, from about 28 mg to about 36 mg, from about 28 mg to about 34 mg, from about 28 mg to about 32 mg, or from about 29 mg to about 31 mg.

Certain embodiments of a pharmaceutical powder composition according to the present disclosure include glidant comprising or consisting of colloidal silicon dioxide. The concentration of colloidal silicon dioxide in various embodiments of a pharmaceutical powder composition according to certain non-limiting embodiments of the present disclosure can range from about 0.5% to about 1.5%, from about 0.6% to about 1.5%, from about 0.75% to about 1.5%, from about 0.8% to about 1.5%, from about 0.9% to about 1.5%, from about 0.5% to about 1.4%, from about 0.5% to about 1.3%, from about 0.5% to about 1.2%, from about 0.5% to about 1.1%, from about 0.75% to about 1.25%, from about 0.85% to about 1.25%, from about 0.85% to about 1.15%, or from about 0.85% to about 1.05%, all in weight percent based on total weight of the pharmaceutical powder composition.

In certain non-limiting embodiments of a pharmaceutical powder composition according to the present disclosure comprising glidant comprising or consisting of colloidal silicon dioxide, the amount of colloidal silicon dioxide included in the pharmaceutical powder composition can range from about 5 mg to about 36 mg, such as from about 5 mg to about 9 mg, from about 5 mg to about 8 mg, from about 6 mg to about 9 mg, from about 6 mg to about 8 mg, from about 7 mg to about 8 mg, from about 12 mg to about 18 mg, from about 12 mg to about 17 mg, from about 12 mg to about 16 mg, from about 13 mg to about 18 mg, from about 14 mg to about 18 mg, from about 13 mg to about 17 mg, from about 13 mg to about 16 mg, from about 14 mg to about 16 mg, from about 24 mg to about 36 mg, from about 24 mg to about 34 mg, from about 24 mg to about 32 mg, from about 26 mg to about 36 mg, from about 26 mg to about 34 mg, from about 26 mg to about 32 mg, from about 28 mg to about 36 mg, from about 28 mg to about 34 mg, from about 28 mg to about 32 mg, or from about 29 mg to about 31 mg.

Various non-limiting embodiments of a pharmaceutical powder composition according to the present disclosure can comprise citric acid. The concentration of citric acid in certain non-limiting embodiments of a pharmaceutical powder composition according to the present disclosure can range from about 0.25% to about 1.0%, from about 0.25% to about 0.75%, from about 0.3% to about 1.0%, from about 0.4% to about 1.0%, from about 0.35% to about 0.75%, or from about 0.4% to about 0.6%, all in weight percent based on total weight of the pharmaceutical powder composition.

The amount of citric acid included in certain non-limiting embodiments of a pharmaceutical powder composition according to the present disclosure can range from about 3 mg to about 20 mg, such as from about 3 mg to about 5 mg, from about 3.5 mg to about 5 mg, from about 3.5 mg to about 4.5 mg, from about 6 mg to about 10 mg, from about 6 mg to about 9 mg, from about 7 mg to about 10 mg, from about 7 mg to about 9 mg, from about 12 mg to about 20 mg, from about 12 mg to about 18 mg, from about 14 mg to about 20 mg, from about 14 mg to about 18 mg, or from about 15 mg to about 17 mg.

In certain non-limiting embodiments, the pharmaceutical powder composition according to the present disclosure can comprise one or more additional excipients, including but not limited to one or more of sweeteners, flavoring agents, coloring agents, and the like.

One or more sweeteners can be included in various non-limiting embodiments of the pharmaceutical powder composition according to the present disclosure. The one or more sweeteners can include any compound or compounds that provide a sweet taste, including, for example, natural sugars, synthetic sugars, natural sweeteners, artificial sweeteners, natural extracts, and any compound that initiates a sweet sensation in a subject. In certain non-limiting embodiments, solid, powdered sweeteners are included in the pharmaceutical powder composition disclosed herein.

Suitable sweeteners for inclusion in embodiments of the pharmaceutical powder compositions according to the present disclosure include, but are not limited to, glucose, fructose, sucrose, xylitol, tagatose, sucralose, maltitol, isomaltulose, isomalt sugar substitute, hydrogenated isomaltulose, lactitol, sorbitol, erythritol, trehalose, maltodextrin, polydextrose, and the like. Other sweeteners that may be included in the pharmaceutical powder compositions herein include, for example, glycerin, inulin, erythritol, maltol, acesulfame and salts thereof (e.g., acesulfame potassium), alitame, aspartame, neotame, sodium cyclamate, saccharin and salts thereof (e.g., saccharin sodium or saccharin calcium), neohesperidin dihydrochalcone, stevioside, thaumatin, and the like. Sweeteners can be used in the form of crude or refined products such as hydrogenated starch hydrolysates, maltitol syrup, high fructose corn syrup, etc., and/or as branded products, e.g., SWEET AM™ liquid (Product Code 918.003—propylene glycol, ethyl alcohol, and proprietary artificial flavor combination, Flavors of North America) and SWEET AM™ powder (Product Code 918.005—maltodextrin, sorbitol, and fructose combination, and Product Code 918.010—water, propylene glycol, sorbitol, fructose, and proprietary natural and artificial flavor combination, Flavors of North America), PROSWEET™ sweetener (1-10% proprietary plant/vegetable extract and 90-99% dextrose combination, Virginia Dare), MALTISWEET™ sweetener (maltitol solution, Ingredion), SORBO™ sweetener (sorbitol and sorbitol/xylitol solution, SPI Polyols), INVERTOSE™ sweetener (high fructose corn syrup, Ingredion), REBALANCE™ M60 and X60 sweeteners (sucralose and maltodextrin, Tate and Lyle), and ORA-SWEET® sugar-free flavored syrup (Paddock Laboratories, Inc.). Sweeteners can be used singularly or in combinations of two or more. Suitable concentrations of different sweeteners can be selected based on published information, manufacturers' data sheets, and through routine testing.

Various non-limiting embodiments of a pharmaceutical powder composition according to the present disclosure can comprise a sweetener in a concentration ranging from about 1.0% to about 3.0%, from about 1.25% to about 3.0%, from about 1.5% to about 3.0%, from about 1.75% to about 3.0%, from about 1.0% to about 2.75%, from about 1.0% to about 2.5%, from about 1.0% to about 2.25%, from about 1.25% to about 2.5%, from about 1.5% to about 2.5%, or from about 1.75% to about 2.25%, all in weight percent based on total weight of the pharmaceutical powder composition.

In certain non-limiting embodiments, the amount of sweetener included in a pharmaceutical powder composition according to the present disclosure can range from about 14 mg to about 80 mg, such as from about 14 mg to about 20 mg, from about 14 mg to about 18 mg, from about 16 mg to about 20 mg, from about 16 mg to about 18 mg, from about 28 mg to about 40 mg, from about 30 mg to about 40 mg, from about 32 mg to about 40 mg, from about 28 mg to about 38 mg, from about 28 mg to about 36 mg, from about 30 mg to about 38 mg, from about 30 mg to about 36 mg, from about 32 mg to about 36 mg, from about 33 mg to about 35 mg, from about 56 mg to about 80 mg, from about 56 mg to about 78 mg, from about 56 mg to about 74 mg, from about 56 mg to about 72 mg, from about 56 mg to about 70 mg, from about 58 mg to about 80 mg, from about 60 mg to about 80 mg, from about 62 mg to about 80 mg, from about 64 mg to about 80 mg, from about 66 mg to about 80 mg, from about 60 mg to about 76 mg, from about 62 mg to about 74 mg, from about 64 mg to about 72 mg, or from about 66 mg to about 70 mg.

Certain non-limiting embodiments of a pharmaceutical powder composition according to the present disclosure can comprise sweetener comprising or consisting of sucralose. The concentration of sucralose in certain embodiments of a pharmaceutical powder composition according to the present disclosure can range from about 1.0% to about 3.0%, from about 1.25% to about 3.0%, from about 1.5% to about 3.0%, from about 1.75% to about 3.0%, from about 1.0% to about 2.75%, from about 1.0% to about 2.5%, from about 1.0% to about 2.25%, from about 1.25% to about 2.5%, from about 1.5% to about 2.5%, or from about 1.75% to about 2.25%, all in weight percent based on total weight of the pharmaceutical powder composition.

In certain non-limiting embodiments of a pharmaceutical powder composition according to the present disclosure comprising sucralose, the amount of sucralose can range from about 14 mg to about 80 mg, such as from about 14 mg to about 20 mg, from about 14 mg to about 18 mg, from about 16 mg to about 20 mg, from about 16 mg to about 18 mg, from about 28 mg to about 40 mg, from about 30 mg to about 40 mg, from about 32 mg to about 40 mg, from about 28 mg to about 38 mg, from about 28 mg to about 36 mg, from about 30 mg to about 38 mg, from about 30 mg to about 36 mg, from about 32 mg to about 36 mg, from about 33 mg to about 35 mg, from about 56 mg to about 80 mg, from about 56 mg to about 78 mg, from about 56 mg to about 74 mg, from about 56 mg to about 72 mg, from about 56 mg to about 70 mg, from about 58 mg to about 80 mg, from about 60 mg to about 80 mg, from about 62 mg to about 80 mg, from about 64 mg to about 80 mg, from about 66 mg to about 80 mg, from about 60 mg to about 76 mg, from about 62 mg to about 74 mg, from about 64 mg to about 72 mg, or from about 66 mg to about 70 mg.

One or more flavoring additives can be used to enhance the taste or aroma of pharmaceutical powder compositions according to the present disclosure. Suitable natural or synthetic flavoring additives can be used, non-limiting examples of which include almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, tutti-frutti, vanilla, wintergreen, and the like. In certain embodiments, a pharmaceutical powder compositions according to the present disclosure includes flavoring additive comprising or consisting of an orange flavoring additive.

Various non-limiting embodiments of a pharmaceutical powder composition according to the present disclosure can comprise one or more flavoring additives. The concentration of flavoring additive in embodiments of a pharmaceutical powder composition according to certain non-limiting embodiments of the present disclosure can range from about 0.5% to about 1.5%, from about 0.6% to about 1.5%, from about 0.75% to about 1.5%, from about 0.8% to about 1.5%, from about 0.9% to about 1.5%, from about 0.5% to about 1.4%, from about 0.5% to about 1.3%, from about 0.5% to about 1.2%, from about 0.75% to about 1.25%, or from about 0.85% to about 1.25%, all in weight percent based on total weight of the pharmaceutical powder composition.

In certain non-limiting embodiments, the amount of flavoring additive included in a pharmaceutical powder composition according to the present disclosure can range from about 7 mg to about 46 mg, such as from about 7 mg to about 11 mg, from about 7 mg to about 10 mg, from about 8 mg to about 11 mg, from about 8 mg to about 10 mg, from about 14 mg to about 22 mg, from about 16 mg to about 22 mg, from about 16 mg to about 20 mg, from about 17 mg to about 19 mg, from about 30 mg to about 46 mg, from about 32 mg to about 46 mg, from about 34 mg to about 46 mg, from about 36 mg to about 46 mg, from about 30 mg to about 44 mg, from about 30 mg to about 42 mg, from about 30 mg to about 40 mg, from about 32 mg to about 42 mg, from about 34 mg to about 42 mg, from about 36 mg to about 42 mg, from about 36 mg to about 40 mg, or from about 37 mg to about 39 mg.

One or more colorants can be included in various non-limiting embodiments of the pharmaceutical powder compositions herein for identification and/or aesthetic purposes. Suitable colorants include, but are not limited to, FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide, and mixtures of any two or more thereof.

In certain non-limiting embodiments according to the present disclosure, a pharmaceutical powder composition comprises potassium chloride and colloidal silicon dioxide. Certain embodiments of the pharmaceutical powder compositions can further comprise one or more sweetener and/or citric acid. In various embodiments, the pharmaceutical powder composition retains at least 90% of an initial potassium chloride content in the pharmaceutical powder composition when the powder is stored for one or more of the following time periods under one or more of the following storage conditions: stored for 3, 6, 9, 12, 18, 24, 36, or 48 months under standard testing conditions (25° C.±2° C. and 60%±5% relative humidity); stored for 1, 2, 3, or 6 months under accelerated testing conditions (40° C.±2° C. and 75%±5% relative humidity).

In certain non-limiting embodiments according to the present disclosure, a pharmaceutical powder composition comprises potassium chloride and colloidal silicon dioxide. Certain embodiments of the pharmaceutical powder compositions can further comprise one or more sweetener and/or citric acid. In various embodiments, the pharmaceutical powder composition retains at least 95% of an initial potassium chloride content in the pharmaceutical powder composition when the powder is stored for one or more of the following time periods under one or more of the following storage conditions: stored for 3, 6, 9, 12, 18, 24, 36, or 48 months under standard testing conditions (25° C.±2° C. and 60%±5% relative humidity); stored for 1, 2, 3, or 6 months under accelerated testing conditions (40° C.±2° C. and 75%±5% relative humidity).

In certain non-limiting embodiments according to the present disclosure, a pharmaceutical powder composition comprises potassium chloride and colloidal silicon dioxide. Certain embodiments of the pharmaceutical powder compositions can further comprise one or more sweetener and/or citric acid. In various embodiments, the pharmaceutical powder composition retains at least 97% of an initial potassium chloride content in the pharmaceutical powder composition when the powder is stored for one or more of the following time periods under one or more of the following storage conditions: stored for 3, 6, 9, 12, 18, 24, 36, or 48 months under standard testing conditions (25° C.±2° C. and 60%±5% relative humidity); stored for 1, 2, 3, or 6 months under accelerated testing conditions (40° C.±2° C. and 75%±5% relative humidity).

In certain non-limiting embodiments according to the present disclosure, a pharmaceutical powder composition comprises potassium chloride and colloidal silicon dioxide. Certain embodiments of the pharmaceutical powder compositions can further comprise one or more sweetener and/or citric acid. In various embodiments, the pharmaceutical powder composition retains at least 99% of an initial potassium chloride content in the pharmaceutical powder composition when the powder is stored for one or more of the following time periods under one or more of the following storage conditions: stored for 3, 6, 9, 12, 18, 24, 36, or 48 months under standard testing conditions (25° C.±2° C. and 60%±5% relative humidity); stored for 1, 2, 3, or 6 months under accelerated testing conditions (40° C.±2° C. and 75%±5% relative humidity).

In certain non-limiting embodiments, pharmaceutical powder compositions according to the present disclosure can be prepared by a method comprising a dry blending process that provides for uniform blending of ingredients. The dry uniform blending of the ingredients can comprise techniques known in the art, such as one or more of blending, mixing, sieving, co-milling, grinding, granulation, and power granulation. The dry blending process can result in a homogenous powder mixture so that packaged amounts of the homogenous powder mixture include a desired mEq amount of potassium chloride.

An additional aspect of the present disclosure is directed to a packaged pharmaceutical powder product comprising a pouch or other suitable container and a predetermined volume of a pharmaceutical powder composition according to the present disclosure sealed in the pouch or other container. In certain non-limiting embodiments of the packaged pharmaceutical product, the pouch or other container can comprise one or more layers selected from a paper layer, a low density polyethylene layer, an aluminum foil barrier layer, and a sealant layer. In certain non-limiting embodiments, the pouch or other container can comprise a paper layer, a low density polyethylene layer, an aluminum foil barrier layer, and a sealant layer. In certain non-limiting embodiments, about 25 to about 35 of the packaged pharmaceutical products comprising the pouch or other container and the volume of pharmaceutical powder composition contained therein are disposed in a carton or other suitable container. In certain other non-limiting embodiments, about 90 to about 110 of the packaged pharmaceutical products comprising the pouch or other container and the volume of pharmaceutical powder composition contained therein are disposed in a carton or other suitable container.

In certain non-limiting embodiments according to the present disclosure, a volume of a pharmaceutical powder composition according to the present disclosure sealed in a pouch as described herein or other container retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 3, 6, 9, 12, 18, 24, 36, or 48 months at about 23° C. to about 27° C. and a relative humidity of about 55% to about 65%. In certain non-limiting embodiments according to the present disclosure, a volume of a pharmaceutical powder composition according to the present disclosure sealed in a pouch as described herein or other container retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 1, 2, 3, or 6 months at about 38° C. to about 42° C. and a relative humidity of about 70% to about 80%.

The present inventors observed that embodiments of pharmaceutical powder composition according to the present disclosure including potassium chloride exhibit advantageous stability of the potassium chloride. For example, the present inventors observed that certain non-limiting embodiments of a pharmaceutical powder composition according to the present disclosure retained at least 90% of an initial amount of potassium chloride after storage for 3 months, 6 months, 9 months, 12 months, 18 months, 24 months, 36 months, or 48 months under standard testing conditions including a temperature of about 23° C. to about 27° C. and a relative humidity from about 55% to about 65%. The present inventors also observed that certain non-limiting embodiments of a pharmaceutical powder composition according to the present disclosure retained at least 90% of an initial amount of potassium chloride after storage for one month, two months, three months, or six months under accelerated testing conditions including a temperature of about 38° C. to about 42° C. and a relative humidity from about 70% to about 80%.

The present inventors also observed that certain non-limiting embodiments of a pharmaceutical powder composition according to the present disclosure retained at least 92% of an initial amount of potassium chloride after storage for 3 months, 6 months, 9 months, 12 months, 18 months, 24 months, 36 months, or 48 months under standard testing conditions including a temperature of about 23° C. to about 27° C. and a relative humidity from about 55% to about 65%. The present inventors also observed that certain embodiments of a pharmaceutical powder composition according to the present disclosure retained at least 92% of an initial amount of potassium chloride after storage for one month, two months, three months, or six months under accelerated testing conditions including a temperature of about 38° C. to about 42° C. and a relative humidity from about 70% to about 80%.

The present inventors observed that certain non-limiting embodiments of a pharmaceutical powder composition according to the present disclosure retained at least 95% of an initial amount of potassium chloride after storage for 3 months, 6 months, 9 months, 12 months, 18 months, 24 months, 36 months, or 48 months under standard testing conditions including a temperature of about 23° C. to about 27° C. and a relative humidity from about 55% to about 65%. The present inventors also observed that certain embodiments of a pharmaceutical powder composition according to the present disclosure retained at least 95% of an initial amount of potassium chloride after storage for one month, two months, three months, or six months under accelerated testing conditions including a temperature of about 38° C. to about 42° C. and a relative humidity from about 70% to about 80%.

The present inventors observed that certain non-limiting embodiments of pharmaceutical powder composition according to the present disclosure retained at least 97% of an initial amount of potassium chloride after storage for 3 months, 6 months, 9 months, 12 months, 18 months, 24 months, 36 months, or 48 months under standard testing conditions including a temperature of about 23° C. to about 27° C. and a relative humidity from about 55% to about 65%. The present inventors also observed that certain embodiments of pharmaceutical powder composition according to the present disclosure retained at least 97% of an initial amount of potassium chloride after storage for one month, two months, three months, or six months under accelerated testing conditions including a temperature of about 38° C. to about 42° C. and a relative humidity from about 70% to about 80%.

The present inventors observed that certain non-limiting embodiments of a pharmaceutical powder composition according to the present disclosure retained at least 99% of an initial amount of potassium chloride after storage for 3 months, 6 months, 9 months, 12 months, 18 months, 24 months, 36 months, or 48 months under standard testing conditions including a temperature of about 23° C. to about 27° C. and a relative humidity from about 55% to about 65%. The present inventors also observed that certain embodiments of a pharmaceutical powder composition according to the present disclosure retained at least 99% of an initial amount of potassium chloride after storage for one month, two months, three months, or six months under accelerated testing conditions including a temperature of about 38° C. to about 42° C. and a relative humidity from about 70% to about 80%.

In certain non-limiting embodiments according to the present disclosure, an aqueous oral composition is provided. The aqueous oral composition can be made by combining water and a pharmaceutical powder composition comprising, by weight, about 90% to about 99.5% potassium chloride and about 0.5% to about 1.5% colloidal silicon dioxide. The aqueous oral composition can be made by combining water and any of the pharmaceutical powder compositions disclosed herein.

Methods of Treatment:

In certain non-limiting embodiments, methods of treatment are provided comprising administering an aqueous oral composition as disclosed herein to a subject in need thereof. In some embodiments, an aqueous oral composition as disclosed herein can be used to treat hypokalemia in a subject. The subject can be a pediatric subject, an adult subject, or a geriatric subject.

Dosing:

Dosages of the aqueous oral compositions disclosed herein can be determined by any suitable method. In various embodiments, the dosage of potassium chloride for treating hypokalemia in adults is about 8 mEq to about 48 mEq potassium chloride per 24 hour period. In certain embodiments of a method according to the present disclosure, the dosage of potassium chloride administered to a subject is about 8 mEq to about 48 mEq potassium, such as about 8 mEq to about 12 mEq potassium chloride, about 8 mEq to about 11 mEq potassium chloride, about 9 mEq to about 12 mEq potassium chloride, about 9 mEq to about 11 mEq potassium chloride, about 16 mEq to about 24 mEq potassium chloride, about 18 mEq to about 24 mEq potassium chloride, about 18 mEq to about 22 mEq potassium chloride, about 16 mEq to about 22 mEq potassium chloride, about 19 mEq to about 21 mEq potassium chloride, about 32 mEq to about 48 mEq potassium chloride, about 34 mEq to about 48 mEq potassium chloride, about 36 mEq to about 48 mEq potassium chloride, about 38 mEq to about 48 mEq potassium chloride, about 32 mEq to about 46 mEq potassium chloride, about 32 mEq to about 44 mEq potassium chloride, about 32 mEq to about 42 mEq potassium chloride, about 34 mEq to about 46 mEq potassium chloride, about 36 mEq to about 44 mEq potassium chloride, about 38 mEq to about 42 mEq potassium chloride, or about 39 mEq to about 41 mEq potassium chloride per 24 hour period. In various non-limiting embodiments, the daily dose is administered over 2 to 5 divided doses, 2 to 4 divided doses, 2 to 3 divided doses, 2 divided doses, 3 divided doses, 4 divided doses, or 5 divided doses. In various non-limiting embodiments, about 45 mEq potassium chloride or less is administered per dose. In certain embodiments, about 45 mEq potassium chloride, about 40 mEq potassium chloride, about 35 mEq potassium chloride, about 30 mEq potassium chloride, about 25 mEq potassium chloride, about 20 mEq potassium chloride, about 15 mEq potassium chloride, about 10 mEq potassium chloride, or about 5 mEq potassium chloride is administered per dose.

Administration:

The aqueous oral compositions disclosed herein can be administered at a dosage described herein or at other appropriate dose levels contemplated by a medical practitioner. In certain embodiments, the aqueous oral compositions described herein are administered for prophylactic and/or therapeutic treatments. In certain therapeutic applications, the aqueous oral compositions are administered to a patient already suffering from a condition, e.g., hypokalemia, in an amount sufficient to cure the condition or at least partially arrest or ameliorate the symptoms, e.g., increase potassium levels. Amounts effective for this use depend on the severity of the condition, previous therapy, the patient's health status, weight, and response to the aqueous oral compositions, and the judgment of the treating physician. Therapeutically effective amounts are optionally determined by methods including, but not limited to, a dose escalation clinical trial.

In certain embodiments wherein the patient's condition does not improve, upon the doctor's discretion, the aqueous oral compositions described herein may be administered chronically, that is, for an extended period of time, including throughout the duration of the patient's life, in order to ameliorate or otherwise control or limit the symptoms of the patient's condition. In other embodiments, administration of the aqueous oral composition continues until complete or partial response of a condition occurs.

In some embodiments, the pharmaceutical powder compositions disclosed herein are diluted with a liquid prior to ingestion by the patient. In various embodiments, the pharmaceutical powder compositions are diluted in water or juice. In certain embodiments, the compositions are diluted in a volume-to-volume ratio of 1 part pharmaceutical powder composition to 40 parts diluent, 1 part pharmaceutical powder composition to 30 parts diluent, 1 part pharmaceutical powder composition to 25 parts diluent, 1 part pharmaceutical powder composition to 20 parts diluent, 1 part pharmaceutical powder composition to 15 parts diluent, 1 part pharmaceutical powder composition to 10 parts diluent, 1 part pharmaceutical powder composition to 8 parts diluent, 1 part pharmaceutical powder composition to 7 parts diluent, 1 part pharmaceutical powder composition to 6 parts diluent, 1 part pharmaceutical powder composition to 5 parts diluent, 1 part pharmaceutical powder composition to 4 parts diluent, 1 part pharmaceutical powder composition to 3 parts diluent, or 1 part pharmaceutical powder composition to 2 parts diluent.

In certain non-limiting embodiments, an aqueous oral composition according to the present disclosure is prepared by mixing or otherwise combining an amount of a pharmaceutical powder composition according to the present disclosure contained in one pouch as described herein or other container with about 4 mL of water.

In some embodiments, the aqueous oral compositions according to the present disclosure are administered to a subject who is in a fed state. A fed state refers to a subject who has taken food or has had a meal. In certain embodiments, the aqueous oral composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain embodiments, the aqueous oral composition is administered to a subject with food.

The following are non-limiting examples of pharmaceutical powder compositions including potassium chloride and methods of making and using the pharmaceutical powder compositions according to the present disclosure.

EXAMPLES

Example 1

This example describes a non-limiting embodiment of a process that may be used to make pharmaceutical powder compositions according to the present disclosure.

A predetermined volume of powdered potassium chloride was screened and added to a 10 $ft^3$ ribbon blender. Predetermined volumes of colloidal silicon dioxide, sucralose, citric acid, and orange flavoring were each subsequently added to the ribbon blender. Next, FD&C Yellow #6 was added to the ribbon blender. The ingredients were then mixed in the ribbon blender for 10 minutes until uniformly combined, thereby forming a mixed powder composition. After the 10 minutes of mixing, a portion of the mixed powder composition was collected from the bottom discharge valve of the ribbon blender and returned to the top of the ribbon blender. The mixed powder composition was further mixed in the ribbon blender for an additional 10 minutes, thereby forming a generally homogeneous pharmaceutical powder composition.

Example 2

Pharmaceutical powder compositions were prepared using the method generally described in Example 1. Each pharmaceutical powder composition included potassium chloride, colloidal silicon dioxide, sucralose, citric acid, natural & artificial orange flavor, and FD&C Yellow #6. Table 1 below provides the mass and weight/weight concentration of the ingredients in individual powder compositions including predetermined mEq amounts of potassium chloride. The mEq amounts of potassium and chloride in each composition was referred to as the "strength" of the individual compositions. All powder composition strengths (10 mEq, 20 mEq, and 40 mEq) listed in Table 1 included the identical ingredients in substantially identical weight percentage concentrations

TABLE 1

| Pharmaceutical powder compositions | | | | |
|---|---|---|---|---|
| Ingredient | All Powder Composition Strengths % w/w | 10 mEq Strength mg/unit dose (pouch) | 20 mEq Strength mg/unit dose (pouch) | 40 mEq Strength mg/unit dose (pouch) |
| Potassium Chloride, USP | 94.937 | 750 | 1500 | 3000 |
| Colloidal Silicon Dioxide, NF | 0.949 | 7.495 | 14.99 | 29.98 |
| Sucralose, NF | 2.168 | 17.125 | 34.25 | 68.50 |
| Citric Acid, anhydrous, USP | 0.506 | 3.995 | 7.99 | 15.98 |
| Natural & Artificial Orange Flavor | 1.187 | 9.375 | 18.75 | 37.50 |
| FD&C Yellow #6 | 0.253 | 2.00 | 4.00 | 8.00 |
| Total | 100.00 | 789.99 | 1579.98 | 3159.96 |

Example 3

Figure 1B:
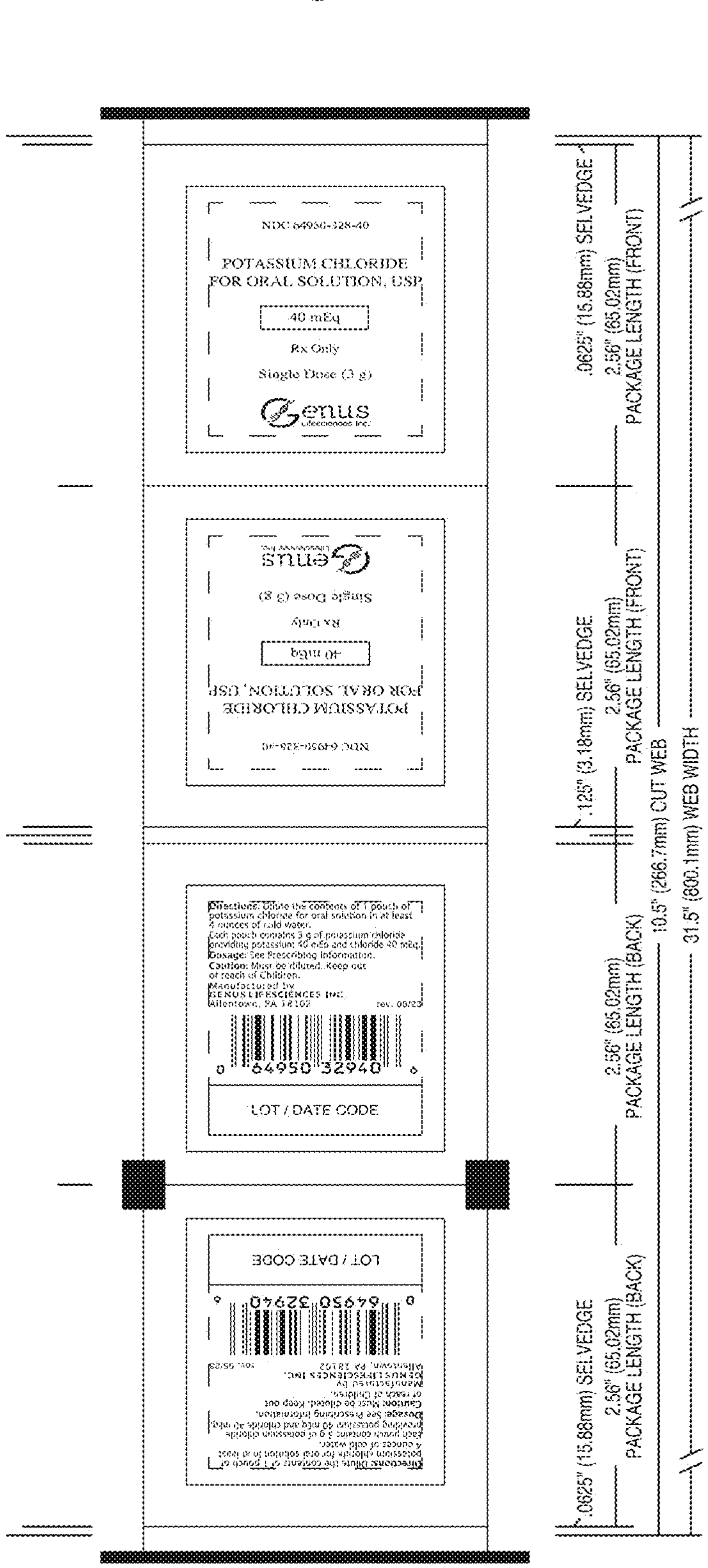
FIG. 1B shows an unassembled container in the form of an unassembled pouch, wherein the pouch is used to contain a pharmaceutical powder composition including about 40 mEq potassium chloride, as described herein.

Measured portions of the pharmaceutical powder compositions described in Example 2 were prepared using the method generally described in Example 1, removed from the ribbon blender, and packaged into individual sealed pouches. The unassembled pouches (Glenroy, Inc., Menomonee Falls, WI) are shown in FIGS. 1A and 1B. The measured portion of pharmaceutical powder composition sealed in a pouch provided a packaged pharmaceutical powder composition.

Each pouch included a 1.60 mil printed paper layer, a 0.50 mil clear low density polyethylene layer, a 0.35 mil aluminum foil barrier layer, and a 1.50 ml SURLYN® polymer sealant layer. The pouch fill weight of the 10 mEq strength pharmaceutical powder composition was 0.79 grams, providing each pouch with 0.75 grams of potassium chloride corresponding to 10 mEq of potassium and 10 mEq of chloride. The pouch fill weight of the 20 mEq strength pharmaceutical powder composition was 1.58 grams, providing each pouch with 1.5 grams of potassium chloride corresponding to 20 mEq of potassium and 20 mEq of chloride. The pouch fill weight of the 40 mEq strength pharmaceutical powder composition was 3.16 grams, providing each pouch with 3.0 grams of potassium chloride corresponding to 40 mEq of potassium and 40 mEq of chloride.

Figure 2A:
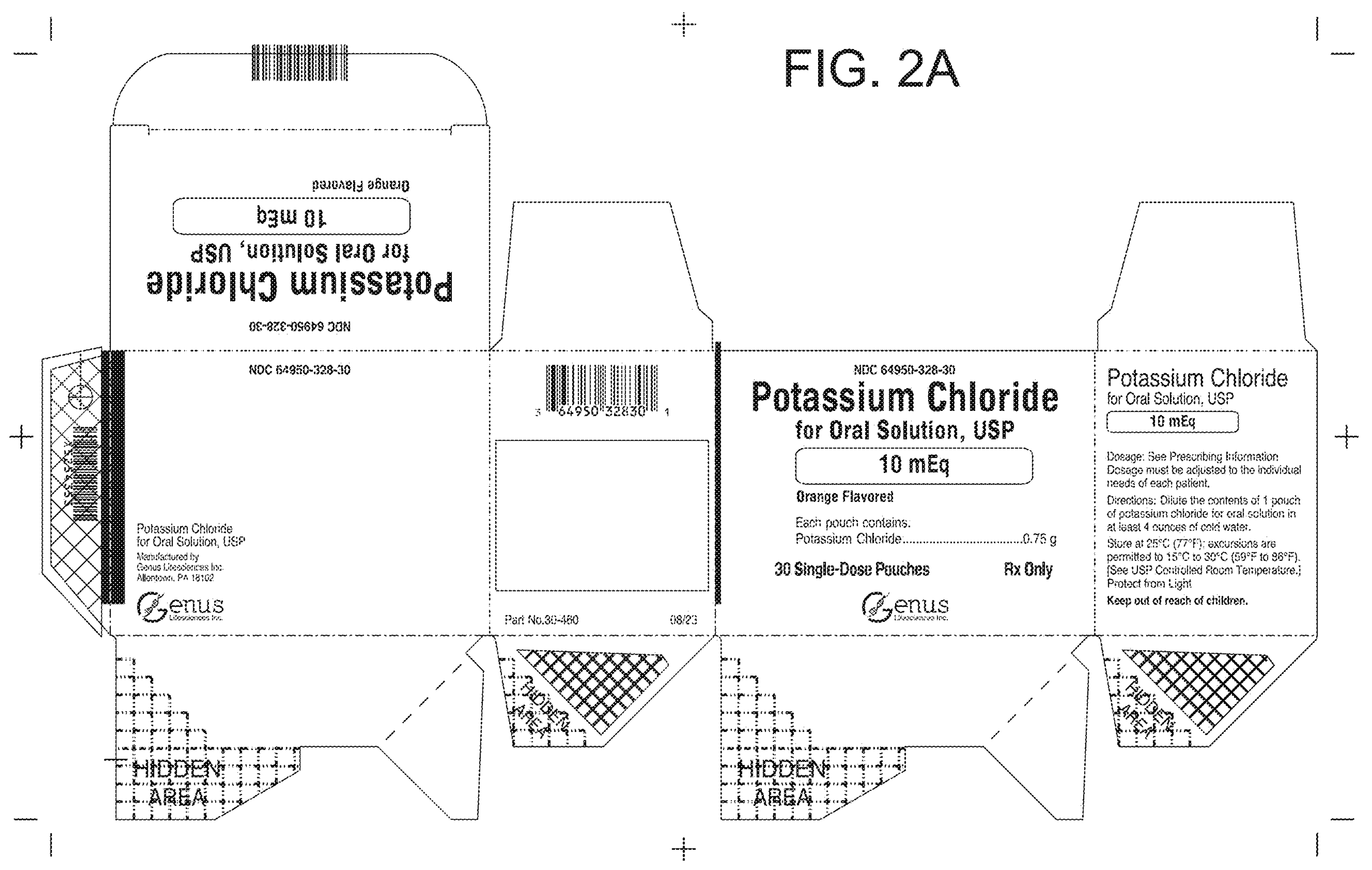
FIG. 2A shows an unassembled carton, wherein the carton is used to contain 30 single-dose pouches containing a pharmaceutical powder composition including about 10 mEq potassium chloride, as described herein.
Figure 2B:
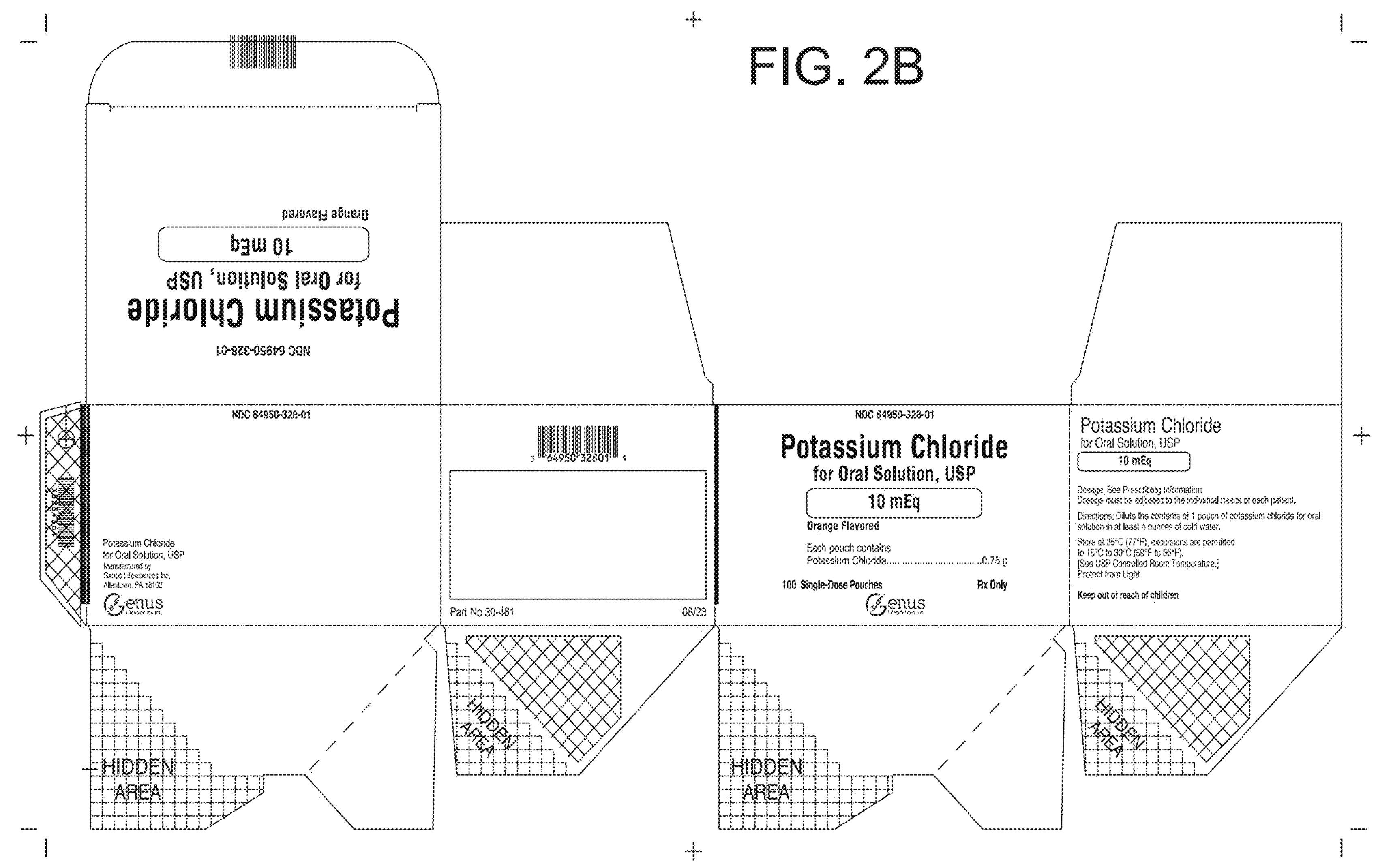
FIG. 2B shows an unassembled carton, wherein the carton is used to contain 100 single-dose pouches containing a pharmaceutical powder composition including about 10 mEq potassium chloride, as described herein.
Figure 3B:
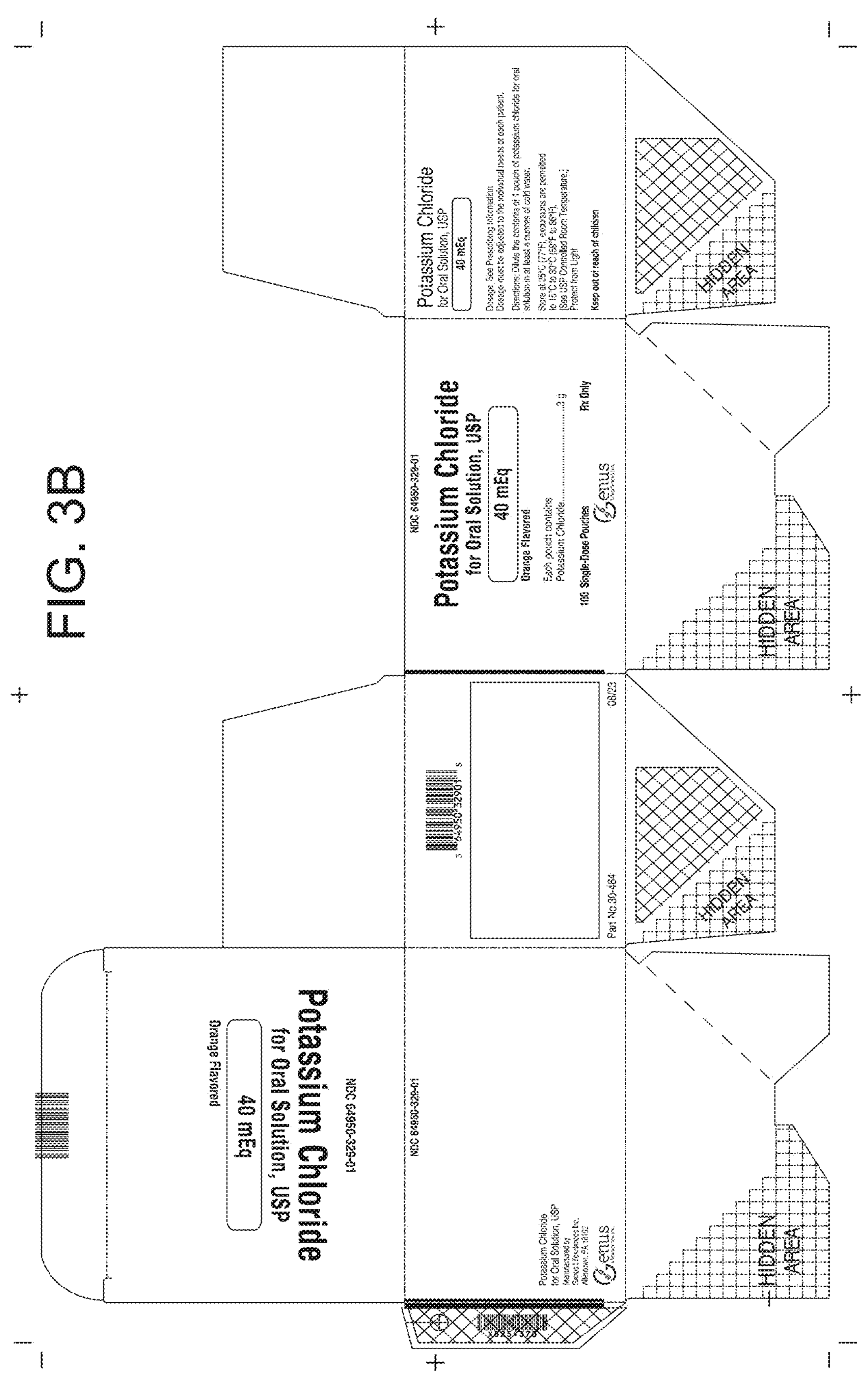
FIG. 3B shows an unassembled carton, wherein the carton is used to contain 100 single-dose pouches containing a pharmaceutical powder composition including about 40 mEq potassium chloride, as described herein.

For storage and distribution purposes, about 25 to about 35 of the pouches can be disposed in the carton shown in an unassembled form in FIGS. 2A and 3A. Also, for storage and distribution purposes, about 90 to about 110 of the pouches can be disposed in the carton shown in an unassembled form in FIGS. 2B and 3B.

Example 4

A study was conducted to assess the stability of embodiments of pharmaceutical powder compositions according to the present disclosure.

Batches of pharmaceutical powder compositions of 10 mEq strength were prepared using the method generally described in Example 1, and predetermined amounts of the powders were individually sealed in the pouches shown in FIGS. 1A and 1B. Table 2 below provides weight/weight concentration of the ingredients in Batches 32800122B, 32800222B, and 32800322B of the pharmaceutical powder compositions of 10 mEq strength and the mass of each ingredient in an individual pouch (i.e., a "unit dose").

TABLE 2

| Pharmaceutical powder composition in Batches 32800122B, 32800222B, and 32800322B | | |
|---|---|---|
| Ingredient | % w/w | mg/unit dose (pouch) |
| Potassium Chloride, USP | 94.937 | 750 |
| Colloidal Silicon Dioxide, NF | 0.949 | 7.495 |
| Sucralose, NF | 2.168 | 17.125 |
| Citric Acid, anhydrous, USP | 0.506 | 3.995 |
| Natural & Artificial Orange Flavor | 1.187 | 9.375 |
| FD&C Yellow #6 | 0.253 | 2.00 |
| Total | 100.00 | 789.99 |

Two studies were conducted to assess the stability of the potassium chloride in the pharmaceutical powder composition produced in Batches 32800122B, 32800222B, and 32800322B in the container system constituting the pouch shown in FIGS. 1A and 1B. The stability studies involved storing the pouches for the following testing periods under the following conditions:

Storing under standard testing conditions (25° C.±2° C. and 60%±5% relative humidity) for up to 9 months.

Storing under accelerated testing conditions (40° C.±2° C. and 75%±5% relative humidity) for up to 6 months.

A standard testing conditions stability study of the pharmaceutical powder composition of Batches 32800122B, 32800222B, and 32800322B contained in the container system was conducted over a period of 9 months to determine the rate of physical or chemical degradation of the potassium chloride included in the pharmaceutical powder composition when stored under the standard environmental conditions for predetermined time periods. Container systems comprising the pouch described above containing the predetermined amount of the pharmaceutical powder composition of 10 mEq strength were placed in a calibrated environmental chamber and maintained at 25° C.±2° C. and 60%±5% relative humidity, uninterrupted (except for the addition or withdrawal of test samples), for a period of 3 months, 6 months or 9 months. Sealed pouches containing the pharmaceutical powder composition were removed from the storage conditions at the specified time points and tested for potassium chloride content using high pressure liquid chromatography.

Considering potassium chloride content, shelf life of the pharmaceutical powder compositions of Batches 32800122B, 32800222B, and 32800322B was estimated to be at least 9 months when stored under standard testing conditions. Table 3 provides the 9 month stability assay results for the pharmaceutical powder compositions of Batches 32800122B, 32800222B, and 32800322B. The stability assay showed that greater than 99 percent of the original potassium chloride content was retained in the pharmaceutical powder compositions stored under standard testing conditions for 9 months.

An accelerated testing conditions stability study of the pharmaceutical powder compositions of Batches 32800122B, 32800222B, and 32800322B contained in the container system was conducted over a period of 6 months to determine the rate of physical or chemical degradation of the potassium chloride included in the pharmaceutical powder compositions when stored under the accelerated environmental conditions. Container systems comprising a pouch as described above containing the predetermined amount of the pharmaceutical powder composition of 10 mEq strength were placed in a calibrated environmental chamber and maintained at 40° C.±2° C. and 75%±5% relative humidity, uninterrupted (except for the addition or withdrawal of test samples), for a period of 1 month, 2 months, 3 months or 6 months. Sealed pouches containing the pharmaceutical powder composition were removed from the storage conditions at the specified time points and tested for potassium chloride content using high pressure liquid chromatography.

Considering potassium chloride content, shelf life of the pharmaceutical powder compositions of Batches 32800122B, 32800222B, and 32800322B was estimated to be at least 6 months when stored under accelerated testing conditions. Table 3 provides the 6 month stability assay results for the pharmaceutical powder compositions of Batches 32800122B, 32800222B, and 32800322B. The stability assay showed that greater than 99 percent of the original potassium chloride content was retained in the pharmaceutical powder compositions stored under accelerated testing conditions for 6 months.

The assay percentages listed in Table 3 are based on the expected original amount of potassium chloride contained in each container system given the make-up of Batches 32800122B, 32800222B, and 32800322B.

TABLE 3

Stability assay results for Batches 32800122B, 32800222B, and 32800322B

| Conditions | Batch | Time (months) | Assay % (Potassium Chloride) |
|---|---|---|---|
| 25° C./60% RH | 32800122B | 0 | 101.2 |
| | 32800122B | 3 | 100.8 |
| | 32800122B | 6 | 100.5 |
| | 32800122B | 9 | 101.8 |
| | 32800222B | 0 | 101.7 |
| | 32800222B | 3 | 101.0 |
| | 32800222B | 6 | 100.5 |
| | 32800222B | 9 | 101.6 |
| | 32800322B | 0 | 101.4 |
| | 32800322B | 3 | 101.6 |
| | 32800322B | 6 | 100.8 |
| | 32800322B | 9 | 101.2 |
| 40° C./75% RH | 32800122B | 0 | 101.2 |
| | 32800122B | 1 | 100.4 |
| | 32800122B | 2 | 100.7 |
| | 32800122B | 3 | 100.5 |
| | 32800122B | 6 | 100.4 |
| | 32800222B | 0 | 101.7 |
| | 32800222B | 1 | 101.1 |
| | 32800222B | 2 | 101.1 |
| | 32800222B | 3 | 101.1 |
| | 32800222B | 6 | 101.2 |
| | 32800322B | 0 | 101.4 |
| | 32800322B | 1 | 100.7 |
| | 32800322B | 2 | 101.6 |
| | 32800322B | 3 | 100.1 |
| | 32800322B | 6 | 101.3 |

With reference to the results shown in Table 3, the present inventors surprisingly observed that the pharmaceutical powder compositions in Batches 32800122B, 32800222B, and 32800322B retained more than about 99% of an original content of potassium chloride when stored under standard testing conditions at 25° C.±2° C. and 60%±5% relative humidity for a period of 9 months. Even when the pharmaceutical powder compositions were stored under accelerated conditions (40° C.±2° C. and 75%±5% relative humidity) for 6 months, the pharmaceutical powder composition in Batches 32800122B, 32800222B, and 32800322B retained over 99% of an original potassium chloride content (a decrease in the potassium chloride content of less than one percent).

Example 5

An additional study was conducted to assess the stability of embodiments of pharmaceutical powder compositions according to the present disclosure.

Batches of pharmaceutical powder compositions of 20 mEq strength were prepared using the method generally described in Example 1, and predetermined amounts of the powders were individually sealed in the pouches shown in FIGS. 1A and 1B. Table 4 below provides weight/weight concentration of the ingredients in Batches 32501718A and 32600218A of the pharmaceutical powder compositions of 20 mEq strength and the mass of each ingredient in an individual pouch (i.e., a "unit dose").

TABLE 4

| Pharmaceutical powder composition in Batches 32501718A and 32600218A | | |
|---|---|---|
| Ingredient | % w/w | mg/unit dose (pouch) |
| Potassium Chloride, USP | 94.937 | 1500 |
| Colloidal Silicon Dioxide, NF | 0.949 | 14.99 |
| Sucralose, NF | 2.168 | 34.25 |
| Citric Acid, anhydrous, USP | 0.506 | 7.99 |
| Natural & Artificial Orange Flavor | 1.187 | 18.75 |
| FD&C Yellow #6 | 0.253 | 4.00 |
| Total | 100.00 | 1579.98 |

Studies were conducted to assess the stability of the potassium chloride in the pharmaceutical powder composition produced in Batches 32501718A and 32600218A. The stability studies involved storing the container systems for the following testing period under the following conditions:

Storing under standard testing conditions (25° C.±2° C. and 60%±5% relative humidity) for up to 48 months.

A standard testing conditions stability study of the pharmaceutical powder compositions of Batches 32501718A and 32600218A contained in the container system was conducted over a period of 48 months to determine the rate of physical or chemical degradation of the potassium chloride included in the pharmaceutical powder compositions when stored under the standard environmental conditions. Container systems comprising a pouch prepared as described above containing pharmaceutical powder composition of 20 mEq strength were placed in a calibrated environmental chamber and maintained at 25° C.±2° C. and 60%±5% relative humidity, uninterrupted (except for the addition or withdrawal of test samples), for a period of 3 months, 6 months, 9 months, 12 months, 18 months, 24 months, 36 months, and 48 months. Sealed pouches were removed from the storage conditions at the specified time points and tested for potassium chloride content using high pressure liquid chromatography.

Considering potassium chloride content, shelf life of the pharmaceutical powder composition of Batches 32501718A and 32600218A was estimated to be at least 48 months when stored under standard testing conditions. Table 5 provides the 48 month stability assay results for the pharmaceutical powder compositions of Batches 32501718A and 32600218A. The stability assay showed that greater than 99 percent of the original potassium chloride content was retained in the pharmaceutical powder compositions stored under standard testing conditions for 48 months.

The assay percentages listed in Table 5 are based on the expected original amount of potassium chloride contained in each container system given the make-up of Batches 32501718A and 32600218A.

TABLE 5

| Stability assay results for Batches 32501718A and 32600218A | | | |
|---|---|---|---|
| Conditions | Batch | Time (months) | Assay % (Potassium Chloride) |
| 25° C./60% | 32501718A | 0 | 101.7 |
| RH | 32501718A | 3 | 100.3 |
| | 32501718A | 6 | 100.6 |
| | 32501718A | 9 | 99.9 |
| | 32501718A | 12 | 102.6 |
| | 32501718A | 18 | 100.3 |
| | 32501718A | 24 | 100.3 |
| | 32501718A | 36 | 100.6 |
| | 32501718A | 48 | 101.6 |
| | 32600218A | 0 | 101.7 |
| | 32600218A | 3 | 100.5 |
| | 32600218A | 6 | 100.8 |
| | 32600218A | 9 | 100.5 |
| | 32600218A | 12 | 100.9 |
| | 32600218A | 18 | 101.0 |
| | 32600218A | 24 | 100.4 |
| | 32600218A | 36 | 100.6 |
| | 32600218A | 48 | 100.8 |

With reference to the results shown in Table 5, the present inventors surprisingly observed that the pharmaceutical powder compositions produced in Batches 32501718A and 32600218A retained more than about 99% of an original content of potassium chloride when stored under standard testing conditions at 25° C.±2° C. and 60%±5% relative humidity for a period of 48 months (a decrease in the potassium chloride content of the pharmaceutical powder composition of less than one percent).

Example 6

A further study was conducted to assess the stability of embodiments of pharmaceutical powder compositions according to the present disclosure.

Several batches of pharmaceutical powder compositions of 40 mEq strength were prepared using the method generally described in Example 1, and predetermined amounts of the powders were individually sealed in the pouches shown in FIGS. 1A and 1B. Table 6 below provides the weight/weight concentrations of the ingredients in Batches 32900122B, 32900222B, and 32900322B of the pharmaceutical powder compositions of 40 mEq strength and the mass of each ingredient in an individual pouch (i.e., a "unit dose").

TABLE 6

| Pharmaceutical powder compositions in Batches 32900122B, 32900222B, and 32900322B | | |
|---|---|---|
| Ingredient | % w/w | mg/unit dose (pouch) |
| Potassium Chloride, USP | 94.937 | 3000 |
| Colloidal Silicon Dioxide, NF | 0.949 | 29.98 |
| Sucralose, NF | 2.168 | 68.50 |
| Citric Acid, anhydrous, USP | 0.506 | 15.98 |
| Natural & Artificial Orange Flavor | 1.187 | 37.50 |
| FD&C Yellow #6 | 0.253 | 8.00 |
| Total | 100.00 | 3159.96 |

Two studies were conducted to assess the stability of the potassium chloride in the pharmaceutical powder composition produced in Batches 32900122B, 32900222B, and 32900322B. The stability studies involved storing the container systems for the following testing period under the following conditions:

Storing under standard testing conditions (25° C.±2° C. and 60%±5% relative humidity) for up to 9 months.

Storing under accelerated testing conditions (40° C.±2° C. and 75%±5% relative humidity) for up to 6 months.

A standard testing conditions stability study of the pharmaceutical powder compositions of Batches 32900122B, 32900222B, and 32900322B contained in the container system was conducted over a period of 9 months to determine the rate of physical or chemical degradation of the potassium chloride included in the pharmaceutical powder composition when stored under the standard conditions. Container systems comprising a pouch as described above containing predetermined amounts of the pharmaceutical powder compositions of 40 mEq strength were placed in a calibrated environmental chamber and maintained at 25° C.±2° C. and 60%±5% relative humidity, uninterrupted (except for the addition or withdrawal of test samples), for a period of 3 months, 6 months or 9 months. Sealed pouches containing the pharmaceutical powder compositions were removed from the storage conditions at the specified time points and tested for potassium chloride content using high pressure liquid chromatography.

Considering potassium chloride content, shelf life of the pharmaceutical powder compositions of Batches 32900122B, 32900222B, and 32900322B was estimated to be at least 9 months when stored under standard testing conditions. Table 7 provides the 9 month stability assay results for the pharmaceutical powder compositions of Batches 32900122B, 32900222B, and 32900322B. The stability assay showed that greater than 99 percent of the original potassium chloride content was retained in the pharmaceutical powder compositions stored under standard testing conditions for 9 months.

An accelerated testing conditions stability study of the pharmaceutical powder compositions of Batches 32900122B, 32900222B, and 32900322B contained in the container system was conducted over a period of 6 months to determine the rate of physical or chemical degradation of the potassium chloride included in the pharmaceutical powder compositions when stored under the accelerated environmental conditions. Container systems comprising a pouch as described above containing predetermined amounts of the pharmaceutical powder compositions of 40 mEq strength were placed in a calibrated environmental chamber and maintained at 40° C.±2° C. and 75%±5% relative humidity, uninterrupted (except for the addition or withdrawal of test samples), for a period of 1 month, 2 months, 3 months or 6 months. Sealed pouches containing the pharmaceutical powder compositions were removed from the storage conditions at the specified time points and tested for potassium chloride content using high pressure liquid chromatography.

Considering potassium chloride content, shelf life of the pharmaceutical powder compositions of Batches 32900122B, 32900222B, and 32900322B was estimated to be at least 6 months when stored under accelerated testing conditions. Table 7 provides the 6 month stability assay results for the pharmaceutical powder compositions of Batches 32900122B, 32900222B, and 32900322B. The stability assay showed that greater than 99 percent of the original potassium chloride content was retained in the pharmaceutical powder composition stored under accelerated testing conditions for 6 months.

The assay percentages listed in Table 7 are based on the expected original amount of potassium chloride contained in each container system given the make-up of Batches 32900122B, 32900222B, and 32900322B.

TABLE 7

Stability assay results for Batches 32900122B, 32900222B, and 32900322B

| Conditions | Batch | Time (months) | Assay % (Potassium Chloride) |
|---|---|---|---|
| 25° C./60% RH | 32900122B | 0 | 100.1 |
| | 32900122B | 3 | 100.3 |
| | 32900122B | 6 | 100.0 |
| | 32900122B | 9 | 100.1 |
| | 32900222B | 0 | 100.6 |
| | 32900222B | 3 | 99.6 |
| | 32900222B | 6 | 100.5 |
| | 32900222B | 9 | 100.9 |
| | 32900322B | 0 | 100.8 |
| | 32900322B | 3 | 101.5 |
| | 32900322B | 6 | 100.4 |
| | 32900322B | 9 | 100.1 |
| 40° C./75% RH | 32900122B | 0 | 100.1 |
| | 32900122B | 1 | 99.4 |
| | 32900122B | 2 | 100.3 |
| | 32900122B | 3 | 100.0 |
| | 32900122B | 6 | 99.7 |
| | 32900222B | 0 | 100.6 |
| | 32900222B | 1 | 100.2 |
| | 32900222B | 2 | 100.4 |
| | 32900222B | 3 | 100.0 |
| | 32900222B | 6 | 100.2 |
| | 32900322B | 0 | 100.8 |
| | 32900322B | 1 | 101.1 |
| | 32900322B | 2 | 100.4 |
| | 32900322B | 3 | 101.3 |
| | 32900322B | 6 | 100.5 |

With reference to the results shown in Table 7, the present inventors surprisingly observed that the pharmaceutical powder compositions produced in Batches 32900122B, 32900222B, and 32900322B retained more than about 99% of the original content of potassium chloride when stored under standard testing conditions at 25° C.±2° C. and 60%±5% relative humidity for a period of 9 months. Even when the pharmaceutical powder compositions were stored under accelerated conditions (40° C.±2° C. and 75%±5% relative humidity) for 6 months, the pharmaceutical powder compositions produced in Batches 32900122B, 32900222B, and 32900322B retained more than 99% of the original potassium chloride content (a decrease in the potassium chloride content of the pharmaceutical powder compositions of less than one percent).

Example 7

A study was conducted to assess the stability of embodiments of pharmaceutical powder compositions according to the present disclosure.

Batches of pharmaceutical powder compositions of 10 mEq strength were prepared using the method generally described in Example 1, and predetermined amounts of the powders were individually sealed in the pouches shown in FIGS. 1A and 1B. Table 8 below provides weight/weight concentrations of the ingredients in Batches 32800122B, 32800222B, and 32800322B of the pharmaceutical powder compositions of 10 mEq strength and the mass of each ingredient in an individual pouch (i.e., a "unit dose").

TABLE 8

| Pharmaceutical powder composition in Batches 32800122B, 32800222B, and 32800322B | | |
|---|---|---|
| Ingredient | % w/w | mg/unit dose (pouch) |
| Potassium Chloride, USP | 94.937 | 750 |
| Colloidal Silicon Dioxide, NF | 0.949 | 7.495 |
| Sucralose, NF | 2.168 | 17.125 |
| Citric Acid, anhydrous, USP | 0.506 | 3.995 |
| Natural & Artificial Orange Flavor | 1.187 | 9.375 |
| FD&C Yellow #6 | 0.253 | 2.00 |
| Total | 100.00 | 789.99 |

Two studies were conducted to assess the stability of the potassium chloride in the pharmaceutical powder composition produced in Batches 32800122B, 32800222B, and 32800322B in the container system constituting the pouch shown in FIGS. 1A and 1B. The stability studies involved storing the pouches for the following testing periods under the following conditions:

Storing under standard testing conditions (25° C.±2° C. and 60%±5% relative humidity) for up to 24 months.

Storing under accelerated testing conditions (40° C.±2° C. and 75%±5% relative humidity) for up to 6 months.

A standard testing conditions stability study of the pharmaceutical powder composition of Batches 32800122B, 32800222B, and 32800322B contained in the container system was conducted over a period of 24 months to determine the rate of physical or chemical degradation of the potassium chloride included in the pharmaceutical powder composition when stored under the standard environmental conditions for predetermined time periods. Container systems comprising the pouch described above containing the predetermined amount of the pharmaceutical powder composition of 10 mEq strength were placed in a calibrated environmental chamber and maintained at 25° C.±2° C. and 60%±5% relative humidity, uninterrupted (except for the addition or withdrawal of test samples), for a period of 3 months, 6 months, 9 months, 12 months, 18 months, or 24 months. Sealed pouches containing the pharmaceutical powder composition were removed from the storage conditions at the specified time points and tested for potassium chloride content using high pressure liquid chromatography.

Considering potassium chloride content, shelf life of the pharmaceutical powder compositions of Batches 32800122B, 32800222B, and 32800322B was estimated to be at least 24 months when stored under standard testing conditions. Table 9 provides the 24-month stability assay results for the pharmaceutical powder compositions of Batches 32800122B, 32800222B, and 32800322B. The stability assay showed that about 99 percent of the original potassium chloride content was retained in the pharmaceutical powder compositions stored under standard testing conditions for 24 months.

An accelerated testing conditions stability study of the pharmaceutical powder compositions of Batches 32800122B, 32800222B, and 32800322B contained in the container system was conducted over a period of 6 months to determine the rate of physical or chemical degradation of the potassium chloride included in the pharmaceutical powder compositions when stored under the accelerated environmental conditions. Container systems comprising a pouch as described above containing the predetermined amount of the pharmaceutical powder composition of 10 mEq strength were placed in a calibrated environmental chamber and maintained at 40° C.±2° C. and 75%±5% relative humidity, uninterrupted (except for the addition or withdrawal of test samples), for a period of 1 month, 2 months, 3 months or 6 months. Sealed pouches containing the pharmaceutical powder composition were removed from the storage conditions at the specified time points and tested for potassium chloride content using high pressure liquid chromatography.

Considering potassium chloride content, shelf life of the pharmaceutical powder compositions of Batches 32800122B, 32800222B, and 32800322B was estimated to be at least 6 months when stored under accelerated testing conditions. Table 9 provides the 6 month stability assay results for the pharmaceutical powder compositions of Batches 32800122B, 32800222B, and 32800322B. The stability assay showed that greater than 99 percent of the original potassium chloride content was retained in the pharmaceutical powder compositions stored under accelerated testing conditions for 6 months.

The assay percentages listed in Table 9 are based on the expected original amount of potassium chloride contained in each container system given the make-up of Batches 32800122B, 32800222B, and 32800322B.

TABLE 9

| Stability assay results for Batches 32800122B, 32800222B, and 32800322B | | | |
|---|---|---|---|
| Conditions | Batch | Time (months) | Assay % (Potassium Chloride) |
| 25° C./60% RH | 32800122B | 0 | 101.2 |
| | 32800122B | 3 | 100.8 |
| | 32800122B | 6 | 100.5 |
| | 32800122B | 9 | 101.8 |
| | 32800122B | 12 | 101.0 |
| | 32800122B | 18 | 101.0 |
| | 32800122B | 24 | 100.1 |
| | 32800222B | 0 | 101.7 |
| | 32800222B | 3 | 101.0 |
| | 32800222B | 6 | 100.5 |
| | 32800222B | 9 | 101.6 |
| | 32800222B | 12 | 101.6 |
| | 32800222B | 18 | 100.9 |
| | 32800222B | 24 | 100.4 |
| | 32800322B | 0 | 101.4 |
| | 32800322B | 3 | 101.6 |
| | 32800322B | 6 | 100.8 |
| | 32800322B | 9 | 101.2 |
| | 32800322B | 12 | 101.1 |
| | 32800322B | 18 | 101.0 |
| | 32800322B | 24 | 100.5 |
| 40° C./75% RH | 32800122B | 0 | 101.2 |
| | 32800122B | 1 | 100.4 |
| | 32800122B | 2 | 100.7 |
| | 32800122B | 3 | 100.5 |
| | 32800122B | 6 | 100.4 |
| | 32800222B | 0 | 101.7 |
| | 32800222B | 1 | 101.1 |
| | 32800222B | 2 | 101.1 |
| | 32800222B | 3 | 101.1 |
| | 32800222B | 6 | 101.2 |
| | 32800322B | 0 | 101.4 |
| | 32800322B | 1 | 100.7 |
| | 32800322B | 2 | 101.6 |
| | 32800322B | 3 | 100.1 |
| | 32800322B | 6 | 101.3 |

With reference to the results shown in Table 9, the present inventors surprisingly observed that the pharmaceutical powder compositions in Batches 32800122B, 32800222B, and 32800322B retained about 99% of an original content of potassium chloride when stored under standard testing conditions at 25° C.±2° C. and 60%±5% relative humidity for a period of 24 months. Even when the pharmaceutical powder compositions were stored under accelerated conditions (40° C.±2° C. and 75%±5% relative humidity) for 6 months, the pharmaceutical powder composition in Batches 32800122B, 32800222B, and 32800322B retained over 99% of an original potassium chloride content (a decrease in the potassium chloride content of less than one percent).

Example 8

A further study was conducted to assess the stability of embodiments of pharmaceutical powder compositions according to the present disclosure.

Several batches of pharmaceutical powder compositions of 40 mEq strength were prepared using the method generally described in Example 1, and predetermined amounts of the powders were individually sealed in the pouches shown in FIGS. 1A and 1B. Table 10 below provides the weight/weight concentrations of the ingredients in Batches 32900122B, 32900222B, and 32900322B of the pharmaceutical powder compositions of 40 mEq strength and the mass of each ingredient in an individual pouch (i.e., a "unit dose").

TABLE 10

| Pharmaceutical powder compositions in Batches 32900122B, 32900222B, and 32900322B | | |
|---|---|---|
| Ingredient | % w/w | mg/unit dose (pouch) |
| Potassium Chloride, USP | 94.937 | 3000 |
| Colloidal Silicon Dioxide, NF | 0.949 | 29.98 |
| Sucralose, NF | 2.168 | 68.50 |
| Citric Acid, anhydrous, USP | 0.506 | 15.98 |
| Natural & Artificial Orange Flavor | 1.187 | 37.50 |
| FD&C Yellow #6 | 0.253 | 8.00 |
| Total | 100.00 | 3159.96 |

Two studies were conducted to assess the stability of the potassium chloride in the pharmaceutical powder composition produced in Batches 32900122B, 32900222B, and 32900322B. The stability studies involved storing the container systems for the following testing period under the following conditions:

Storing under standard testing conditions (25° C.±2° C. and 60%±5% relative humidity) for up to 24 months.

Storing under accelerated testing conditions (40° C.±2° C. and 75%±5% relative humidity) for up to 6 months.

A standard testing conditions stability study of the pharmaceutical powder compositions of Batches 32900122B, 32900222B, and 32900322B contained in the container system was conducted over a period of 24 months to determine the rate of physical or chemical degradation of the potassium chloride included in the pharmaceutical powder composition when stored under the standard conditions. Container systems comprising a pouch as described above containing predetermined amounts of the pharmaceutical powder compositions of 40 mEq strength were placed in a calibrated environmental chamber and maintained at 25° C.±2° C. and 60%±5% relative humidity, uninterrupted (except for the addition or withdrawal of test samples), for a period of 3 months, 6 months, 9 months, 12 months, 18 months, or 24 months. Sealed pouches containing the pharmaceutical powder compositions were removed from the storage conditions at the specified time points and tested for potassium chloride content using high pressure liquid chromatography.

Considering potassium chloride content, shelf life of the pharmaceutical powder compositions of Batches 32900122B, 32900222B, and 32900322B was estimated to be at least 24 months when stored under standard testing conditions. Table 11 provides the 24-month stability assay results for the pharmaceutical powder compositions of Batches 32900122B, 32900222B, and 32900322B. The stability assay showed that about 98 percent of the original potassium chloride content was retained in the pharmaceutical powder compositions stored under standard testing conditions for 24 months.

An accelerated testing conditions stability study of the pharmaceutical powder compositions of Batches 32900122B, 32900222B, and 32900322B contained in the container system was conducted over a period of 6 months to determine the rate of physical or chemical degradation of the potassium chloride included in the pharmaceutical powder compositions when stored under the accelerated environmental conditions. Container systems comprising a pouch as described above containing predetermined amounts of the pharmaceutical powder compositions of 40 mEq strength were placed in a calibrated environmental chamber and maintained at 40° C.±2° C. and 75%±5% relative humidity, uninterrupted (except for the addition or withdrawal of test samples), for a period of 1 month, 2 months, 3 months or 6 months. Sealed pouches containing the pharmaceutical powder compositions were removed from the storage conditions at the specified time points and tested for potassium chloride content using high pressure liquid chromatography.

Considering potassium chloride content, shelf life of the pharmaceutical powder compositions of Batches 32900122B, 32900222B, and 32900322B was estimated to be at least 6 months when stored under accelerated testing conditions. Table 11 provides the 6 month stability assay results for the pharmaceutical powder compositions of Batches 32900122B, 32900222B, and 32900322B. The stability assay showed that greater than 99 percent of the original potassium chloride content was retained in the pharmaceutical powder composition stored under accelerated testing conditions for 6 months.

The assay percentages listed in Table 11 are based on the expected original amount of potassium chloride contained in each container system given the make-up of Batches 32900122B, 32900222B, and 32900322B.

TABLE 11

| Stability assay results for Batches 32900122B, 32900222B, and 32900322B | | | |
|---|---|---|---|
| Conditions | Batch | Time (months) | Assay % (Potassium Chloride) |
| 25° C./60% RH | 32900122B | 0 | 100.1 |
| | 32900122B | 3 | 100.3 |
| | 32900122B | 6 | 100.0 |
| | 32900122B | 9 | 100.1 |
| | 32900122B | 12 | 100.6 |
| | 32900122B | 18 | 100.3 |

TABLE 11-continued

| Stability assay results for Batches 32900122B, 32900222B, and 32900322B | | | |
|---|---|---|---|
| Conditions | Batch | Time (months) | Assay % (Potassium Chloride) |
| | 32900122B | 24 | 99.6 |
| | 32900222B | 0 | 100.6 |
| | 32900222B | 3 | 99.6 |
| | 32900222B | 6 | 100.5 |
| | 32900222B | 9 | 100.9 |
| | 32900222B | 12 | 100.3 |
| | 32900222B | 18 | 100.3 |
| | 32900222B | 24 | 98.7 |
| | 32900322B | 0 | 100.8 |
| | 32900322B | 3 | 101.5 |
| | 32900322B | 6 | 100.4 |
| | 32900322B | 9 | 100.1 |
| | 32900322B | 12 | 99.4 |
| | 32900322B | 18 | 100.0 |
| | 32900322B | 24 | 99.1 |
| 40° C./75% RH | 32900122B | 0 | 100.1 |
| | 32900122B | 1 | 99.4 |
| | 32900122B | 2 | 100.3 |
| | 32900122B | 3 | 100.0 |
| | 32900122B | 6 | 99.7 |
| | 32900222B | 0 | 100.6 |
| | 32900222B | 1 | 100.2 |
| | 32900222B | 2 | 100.4 |
| | 32900222B | 3 | 100.0 |
| | 32900222B | 6 | 100.2 |
| | 32900322B | 0 | 100.8 |
| | 32900322B | 1 | 101.1 |
| | 32900322B | 2 | 100.4 |
| | 32900322B | 3 | 101.3 |
| | 32900322B | 6 | 100.5 |

With reference to the results shown in Table 11, the present inventors surprisingly observed that the pharmaceutical powder compositions produced in Batches 32900122B, 32900222B, and 32900322B retained about 98% of the original content of potassium chloride when stored under standard testing conditions at 25° C.±2° C. and 60%±5% relative humidity for a period of 24 months. Even when the pharmaceutical powder compositions were stored under accelerated conditions (40° C.±2° C. and 75%±5% relative humidity) for 6 months, the pharmaceutical powder compositions produced in Batches 32900122B, 32900222B, and 32900322B retained more than 99% of the original potassium chloride content (a decrease in the potassium chloride content of the pharmaceutical powder compositions of less than one percent).

The following numbered clauses are directed to various non-limiting embodiments of inventions according to the present disclosure:

1. A pharmaceutical powder composition comprising, by weight:

about 90% to about 99.5% potassium chloride; and about 0.5% to about 1.5% colloidal silicon dioxide.

2. The pharmaceutical powder composition of Clause 1, comprising, by weight, about 92.5% to about 97.5% potassium chloride.

3. The pharmaceutical powder composition of any of Clauses 1 or 2, comprising, by weight, about 0.75% to about 1.25% colloidal silicon dioxide.

4. The pharmaceutical powder composition of any of Clauses 1-3, further comprising a sweetener.

5. The pharmaceutical powder composition of any of Clauses 1-3, further comprising, by weight, about 1% to about 3% sucralose.

6. The pharmaceutical powder composition of any of Clauses 1-5, further comprising, by weight, about 0.25% to about 1% citric acid.

7. The pharmaceutical powder composition of any of Clauses 1-6, comprising, by weight:

about 92.5% to about 97.5% potassium chloride;

about 0.75% to about 1.25% colloidal silicon dioxide;

about 1% to about 3% sucralose; and about 0.25% to about 1% citric acid.

8. The pharmaceutical powder composition of any of Clauses 1-7, further comprising a flavoring additive.

9. The pharmaceutical powder composition of any of Clauses 1-7, further comprising an orange flavoring additive.

10. The pharmaceutical powder composition of any of Clauses 1-9, further comprising a colorant.

11. The pharmaceutical powder composition of any of Clauses 1-9, further comprising FD&C Yellow #6.

12. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 6 months at about 23° C. to about 27° C. and a relative humidity of about 55% to about 65%.

13. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 9 months at about 23° C. to about 27° C. and a relative humidity of about 55% to about 65%.

14. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 24 months at about 23° C. to about 27° C. and a relative humidity of about 55% to about 65%.

15. The pharmaceutical powder composition of any of Clauses 1-11 provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 36 months at about 23° C. to about 27° C. and a relative humidity of about 55% to about 65%.

16. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 48 months at about 23° C. to about 27° C. and a relative humidity of about 55% to about 65%.

17. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 3 months at about 38° C. to about 42° C. and a relative humidity of about 70% to about 80%.

18. The pharmaceutical powder composition of any of Clauses 1-11, provided that a potassium chloride content in the pharmaceutical powder composition is at least 90%, at least 92%, at least 95%, at least 97%, or at least 99% of an initial potassium chloride content in the pharmaceutical powder composition after the pharmaceutical powder composition has been stored for 6 months at about 38° C. to about 42° C. and a relative humidity of about 70% to about 80%.

19. The pharmaceutical powder composition of any of Clauses 1-11, provided that when a volume of the pharmaceutical powder composition is sealed in a pouch, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 6 months at about 23° C. to about 27° C. and a relative humidity of about 55% to about 65%.

20. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 9 months at about 23° C. to about 27° C. and a relative humidity of about 55% to about 65%.

21. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 24 months at about 23° C. to about 27° C. and a relative humidity of about 55% to about 65%.

22. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 36 months at about 23° C. to about 27° C. and a relative humidity of about 55% to about 65%.

23. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 48 months at about 23° C. to about 27° C. and a relative humidity of about 55% to about 65%.

24. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 3 months at about 38° C. to about 42° C. and a relative humidity of about 70% to about 80%.

25. The pharmaceutical powder composition of any of Clauses 1-11, provided that when a volume of the pharmaceutical powder composition is sealed in a pouch or other container, the volume of the pharmaceutical powder composition retains at least 90%, at least 92%, at least 95%, at least 97%, or at least 99% of an initial potassium chloride content in the volume of the pharmaceutical powder composition after the pouch or other container containing the volume of the pharmaceutical powder composition has been stored for 6 months at about 38° C. to about 42° C. and a relative humidity of about 70% to about 80%.

26. The pharmaceutical powder composition of any of Clauses 19-25, wherein the pouch or other container comprises at least one of a paper layer, a low density polyethylene layer, an aluminum foil barrier layer, and a sealant layer.

27. The pharmaceutical powder composition of any of Clauses 19-25, wherein the pouch or other container comprises a paper layer, a low density polyethylene layer, an aluminum foil barrier layer, and a sealant layer.

28. The pharmaceutical powder composition of any of Clauses 19-27, wherein about 25 to about 35 of the pouches are disposed in a carton.

29. The pharmaceutical powder composition of any of Clauses 19-27, wherein about 90 to about 110 of the pouches are disposed in a carton.

30. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition sealed in the pouch or other container retains at least 90%, at least 92%, at least 95%, at least 97%, or at least 99% of an initial potassium chloride content after the pouch or other container containing the volume of the pharmaceutical powder composition has been stored for 6 months at about 23° C. to about 27° C. and a relative humidity of about 55% to about 65%.

31. The packaged pharmaceutical powder product of Clause 30, wherein the pharmaceutical powder composition has a composition as recited in any of Clauses 2-25.

32. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 9 months at about 23° C. to about 27° C. and a relative humidity of about 55% to about 65%.

33. The packaged pharmaceutical powder product of Clause 32, wherein the pharmaceutical powder composition has a composition as recited in any of Clauses 2-25.

34. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 24 months at about 23° C. to about 27° C. and a relative humidity of about 55% to about 65%.

35. The packaged pharmaceutical powder product of Clause 34, wherein the pharmaceutical powder composition has a composition as recited in any of Clauses 2-25.

36. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 36 months at about 23° C. to about 27° C. and a relative humidity of about 55% to about 65%.

37. The packaged pharmaceutical powder product of Clause 36, wherein the pharmaceutical powder composition has a composition as recited in any of Clauses 2-25.

38. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 48 months at about 23° C. to about 27° C. and a relative humidity of about 55% to about 65%.

39. The packaged pharmaceutical powder product of Clause 38, wherein the pharmaceutical powder composition has a composition as recited in any of Clauses 2-25.

40. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 3 months at about 38° C. to about 42° C. and a relative humidity of about 70% to about 80%.

41. The packaged pharmaceutical powder product of Clause 40, wherein the pharmaceutical powder composition has a composition as recited in any of Clauses 2-25.

42. A packaged pharmaceutical powder product comprising:

a pharmaceutical powder composition comprising, by weight, about 90% to about 99.5% potassium chloride, and about 0.5% to about 1.5% colloidal silicon dioxide; and a pouch or other container;

provided that a volume of the pharmaceutical powder composition is sealed in the pouch or other container; and provided that the volume of the pharmaceutical powder composition enclosed in the pouch or other container retains at least 90%, at least 92%, at least 95%, at least 97%, or at least 99% of an initial potassium chloride content after the pouch or other container containing the volume of the pharmaceutical powder composition has been stored for 6 months at about 38° C. to about 42° C. and a relative humidity of about 70% to about 80%.

43. The packaged pharmaceutical powder product of Clause 42, wherein the pharmaceutical powder composition has a composition as recited in any of Clauses 2-25.

44. An aqueous oral composition made by combining ingredients comprising:

a pharmaceutical powder composition comprising, by weight, about 90% to about 99.5% potassium chloride, and about 0.5% to about 1.5% colloidal silicon dioxide; and water.

45. The aqueous oral composition of Clause 44, wherein the pharmaceutical powder composition comprises, by weight, about 92.5% to about 97.5% potassium chloride.

46. The aqueous oral composition of any of Clauses 44 or 45, wherein the pharmaceutical powder composition comprises, by weight, about 0.75% to about 1.25% colloidal silicon dioxide.

47. The aqueous oral composition of any of Clauses 44-46, wherein the pharmaceutical powder composition further comprises a sweetener.

48. The aqueous oral composition of any of Clauses 44-46, wherein the pharmaceutical powder composition further comprises, by weight, about 1% to about 3% sucralose.

49. The aqueous oral solution of any of Clauses 44-48, wherein the pharmaceutical powder composition further comprises, by weight, about 0.25% to about 1% citric acid.

50. The aqueous oral composition of any of Clauses 44-49, wherein the pharmaceutical powder composition comprises, by weight:

about 92.5% to about 97.5% potassium chloride;
about 0.75% to about 1.25% colloidal silicon dioxide;
about 1% to about 3% sucralose; and
about 0.25% to about 1% citric acid.

51. The aqueous oral composition of any of Clauses 44-50, wherein the pharmaceutical powder composition further comprises a flavoring additive.

52. The aqueous oral composition of any of Clauses 44-51, wherein the pharmaceutical powder composition further comprises a colorant.

53. The aqueous oral composition of Clause 44, wherein the pharmaceutical powder composition has a composition as recited in any of Clauses 2-25.

54. A method for treating hypokalemia, the method comprising administering an effective amount of an aqueous oral solution to a subject in need thereof, wherein the aqueous oral solution is made by combining ingredients comprising:

a pharmaceutical powder composition comprising, by weight,
about 90% to about 99.5% potassium chloride, and
about 0.5% to about 1.5% colloidal silicon dioxide, and
water.

55. A method for treating hypokalemia, the method comprising administering to a subject in need thereof an effective amount of the aqueous oral composition of any of Clauses 44-53.

What is claimed is:

1. A pharmaceutical powder composition comprising, by weight:

about 92.5% to about 97.5% potassium chloride;
about 0.75% to about 1.25% colloidal silicon dioxide;
about 1% to about 3% sweetener; and
about 0.25% to about 1% citric acid.

2. The pharmaceutical powder composition of claim 1, wherein the sweetener comprises sucralose.

3. The pharmaceutical powder composition of claim 1, further comprising a flavoring additive.

4. The pharmaceutical powder composition of claim 1, further comprising an orange flavoring additive.

5. The pharmaceutical powder composition of claim 1, further comprising a colorant.

6. The pharmaceutical powder composition of claim 1, further comprising FD&C Yellow 6.

7. The pharmaceutical powder composition of claim 1, provided that a potassium chloride content in the pharmaceutical powder composition is at least 90% of an initial potassium chloride content in the pharmaceutical powder composition after the pharmaceutical powder composition has been stored for 6 months at about 23° C. to about 27° C. and a relative humidity of about 55% to about 65%.

8. The pharmaceutical powder composition of claim 1, provided that a potassium chloride content in the pharmaceutical powder composition is at least 90% of an initial potassium chloride content in the pharmaceutical powder composition after the pharmaceutical powder composition has been stored for 9 months at about 23° C. to about 27° C. and a relative humidity of about 55% to about 65%.

9. The pharmaceutical powder composition of claim 1, provided that a potassium chloride content in the pharmaceutical powder composition is at least 90% of an initial potassium chloride content in the pharmaceutical powder composition after the pharmaceutical powder composition has been stored for 24 months at about 23° C. to about 27° C. and a relative humidity of about 55% to about 65%.

10. The pharmaceutical powder composition of claim 1, provided that a potassium chloride content in the pharmaceutical powder composition is at least 90% of an initial potassium chloride content in the pharmaceutical powder composition after the pharmaceutical powder composition has been stored for 36 months at about 23° C. to about 27° C. and a relative humidity of about 55% to about 65%.

11. The pharmaceutical powder composition of claim 1, provided that a potassium chloride content in the pharmaceutical powder composition is at least 90% of an initial potassium chloride content in the pharmaceutical powder composition after the pharmaceutical powder composition has been stored for 6 months at about 38° C. to about 42° C. and a relative humidity of about 70% to about 80%.

12. The pharmaceutical powder composition of claim 1, provided that when a volume of the pharmaceutical powder composition is sealed in a pouch, the volume of the pharmaceutical powder composition retains at least 90% of an initial potassium chloride content in the volume of the pharmaceutical powder composition after the pouch containing the volume of the pharmaceutical powder composition has been stored for 24 months at about 23° C. to about 27° C. and a relative humidity of about 55% to about 65%.

13. The pharmaceutical powder composition of claim 1, provided that when a volume of the pharmaceutical powder composition is sealed in a pouch, the volume of the pharmaceutical powder composition retains at least 90% of an initial potassium chloride content in the volume of the pharmaceutical powder composition after the pouch containing the volume of the pharmaceutical powder composition has been stored for 6 months at about 38° C. to about 42° C. and a relative humidity of about 70% to about 80%.

14. The pharmaceutical powder composition of claim 12, wherein the pouch comprises a paper layer, a low density polyethylene layer, an aluminum foil barrier layer, and a sealant layer.

15. A packaged pharmaceutical powder product comprising:

the pharmaceutical powder composition recited in claim 1; and
a pouch;
provided that a volume of the pharmaceutical powder composition is sealed in the pouch; and
provided that the volume of the pharmaceutical powder composition sealed in the pouch retains at least 90% of an initial potassium chloride content after the pouch containing the volume of the pharmaceutical powder composition has been stored for 6 months at about 23° C. to about 27° C. and a relative humidity of about 55% to about 65%.

16. The packaged pharmaceutical powder product of claim 15, wherein the pharmaceutical powder composition comprises, by weight:

about 92.5% to about 97.5% potassium chloride;
about 0.75% to about 1.25% colloidal silicon dioxide;
about 1% to about 3% sucralose; and
about 0.25% to about 1% citric acid.

17. A pharmaceutical powder composition comprising, by weight:

about 92.5% to about 97.5% potassium chloride;
about 0.75% to about 1.25% colloidal silicon dioxide;
about 1% to about 3% sucralose;
about 0.25% to about 1% citric acid;
flavoring additive; and
colorant.

* * * * *